(12) United States Patent
Allen, Sr. et al.

(10) Patent No.: US 9,183,738 B1
(45) Date of Patent: Nov. 10, 2015

(54) WIRELESS THERMOMETER AND METHOD OF USE THEREOF

(71) Applicant: iDevices, LLC, Avon, CT (US)

(72) Inventors: Christopher J. Allen, Sr., West Hartford, CT (US); Shawn Monteith, Burlington, CT (US)

(73) Assignee: IDEVICES, LLC, Avon, CT (US)

( * ) Notice: Subject to any disclaimer, the term of this patent is extended or adjusted under 35 U.S.C. 154(b) by 1 day.

(21) Appl. No.: 13/867,028

(22) Filed: Apr. 19, 2013

Related U.S. Application Data

(60) Provisional application No. 61/635,847, filed on Apr. 19, 2012.

(51) Int. Cl.
| | | |
|---|---|---|
| G08B 23/00 | (2006.01) | |
| G08C 15/06 | (2006.01) | |
| G08C 17/02 | (2006.01) | |
| G01K 13/00 | (2006.01) | |
| G01K 1/02 | (2006.01) | |
| A61B 5/01 | (2006.01) | |

(52) U.S. Cl.
CPC . *G08C 17/02* (2013.01); *A61B 5/01* (2013.01); *G01K 1/024* (2013.01); *G01K 13/002* (2013.01); *A61B 2560/0412* (2013.01)

(58) Field of Classification Search
CPC ....... G01K 13/002; G01K 1/024; A61B 5/01; A61B 2560/0412
USPC ......... 340/870.02, 870.17; 374/110; 600/474, 600/549
See application file for complete search history.

(56) References Cited

U.S. PATENT DOCUMENTS

| | | |
|---|---|---|
| 6,300,871 B1 | 10/2001 | Irwin et al. |
| 6,398,727 B1 | 6/2002 | Bui et al. |
| 6,458,087 B1 | 10/2002 | Al-Rasheed et al. |
| 6,646,567 B1 | 11/2003 | Olivas et al. |
| 6,847,912 B2 | 1/2005 | Forster |
| 6,937,148 B2 | 8/2005 | Irwin |
| 7,004,910 B2 | 2/2006 | Lindsey |
| 7,249,883 B2 * | 7/2007 | Kuroda et al. ................ 374/110 |
| 7,336,153 B2 | 2/2008 | Malone et al. |
| 7,382,247 B2 | 6/2008 | Welch et al. |
| 7,625,117 B2 | 12/2009 | Haslett et al. |
| 7,782,193 B2 | 8/2010 | Goh et al. |
| 7,846,397 B2 | 12/2010 | Gregg et al. |
| 8,043,002 B2 | 10/2011 | Kim et al. |
| 8,160,836 B2 | 4/2012 | Pompei et al. |
| 8,185,341 B2 * | 5/2012 | Yarden et al. ................ 702/128 |

(Continued)

OTHER PUBLICATIONS

Finvers, Ivars G., et al., "Wireless Temporal Artery Bandage Thermometer" © 2006 IEEE.

(Continued)

*Primary Examiner* — John A Tweel, Jr.
(74) *Attorney, Agent, or Firm* — McCarter & English, LLP

(57) ABSTRACT

An apparatus and method for sensing body temperature and wirelessly communicating measured data to at least one electronic device. The device includes a sensor device having a housing base, a housing cover releasably mountable on the housing base, and components for sensing body temperature and wirelessly communicating the measured temperature, including a temperature sensor, a power supply, a microprocessor, and a transmitter and receiver. The electronic device can include an application that communicates with the sensor device and provides a user interface.

39 Claims, 23 Drawing Sheets

(56) References Cited

U.S. PATENT DOCUMENTS

| | | | |
|---|---|---|---|
| 8,296,493 B1 | 10/2012 | Englehardt et al. | |
| 8,573,843 B2 * | 11/2013 | Tsuchida | 374/112 |
| 8,659,421 B2 * | 2/2014 | Babineau | 340/539.15 |
| 8,663,106 B2 * | 3/2014 | Stivoric et al. | 600/301 |
| 8,931,400 B1 | 1/2015 | Allen | |
| 2002/0077766 A1 | 6/2002 | Mault | |
| 2002/0124295 A1 * | 9/2002 | Fenwick et al. | 2/69 |
| 2003/0202558 A1 | 10/2003 | Chung et al. | |
| 2004/0041714 A1 | 3/2004 | Forster | |
| 2004/0116822 A1 | 6/2004 | Lindsey | |
| 2005/0101843 A1 | 5/2005 | Quinn et al. | |
| 2005/0154327 A1 | 7/2005 | Nakazawa | |
| 2005/0226310 A1 | 10/2005 | Nakazawa et al. | |
| 2005/0245839 A1 | 11/2005 | Stivoric et al. | |
| 2006/0122466 A1 | 6/2006 | Nguyen-Dobinsky et al. | |
| 2006/0122473 A1 | 6/2006 | Kill et al. | |
| 2007/0001850 A1 | 1/2007 | Malone et al. | |
| 2007/0041424 A1 | 2/2007 | Lev et al. | |
| 2007/0080223 A1 | 4/2007 | Japuntich | |
| 2007/0206655 A1 | 9/2007 | Haslett et al. | |
| 2008/0018480 A1 | 1/2008 | Sham | |
| 2008/0027288 A1 | 1/2008 | Renz | |
| 2008/0161715 A1 | 7/2008 | Stivoric et al. | |
| 2008/0167572 A1 | 7/2008 | Stivoric et al. | |
| 2008/0167573 A1 | 7/2008 | Stivoric et al. | |
| 2008/0214949 A1 | 9/2008 | Stivoric et al. | |
| 2008/0224852 A1 | 9/2008 | Dicks et al. | |
| 2008/0262781 A1 | 10/2008 | Valdes | |
| 2008/0262782 A1 | 10/2008 | Pompei et al. | |
| 2008/0287768 A1 | 11/2008 | Kuo et al. | |
| 2009/0092522 A1 | 4/2009 | Gregg et al. | |
| 2009/0102611 A1 | 4/2009 | Quinn et al. | |
| 2009/0216090 A1 | 8/2009 | Chen | |
| 2009/0221888 A1 | 9/2009 | Wijesiriwardana | |
| 2010/0004191 A1 | 1/2010 | Hebert | |
| 2010/0006562 A1 | 1/2010 | Clothier | |
| 2010/0044582 A1 | 2/2010 | Cooper et al. | |
| 2010/0044588 A1 | 2/2010 | Park | |
| 2010/0185711 A1 | 7/2010 | Subramaniam | |
| 2010/0220766 A1 | 9/2010 | Burgard | |
| 2011/0015496 A1 | 1/2011 | Sherman et al. | |
| 2011/0066533 A1 | 3/2011 | O'Brien et al. | |
| 2011/0078441 A1 | 3/2011 | Dicks et al. | |
| 2011/0115633 A1 | 5/2011 | Morris et al. | |
| 2011/0137141 A1 | 6/2011 | Razoumov et al. | |
| 2011/0158284 A1 | 6/2011 | Goto | |
| 2011/0190030 A1 | 8/2011 | Glynn | |
| 2011/0276345 A1 | 11/2011 | Wang et al. | |
| 2011/0280279 A1 | 11/2011 | Gregory et al. | |
| 2011/0291827 A1 | 12/2011 | Baldocchi et al. | |
| 2011/0302050 A1 | 12/2011 | Kildevaeld | |
| 2012/0003933 A1 | 1/2012 | Baker et al. | |
| 2012/0050047 A1 | 3/2012 | Kim et al. | |
| 2012/0053424 A1 | 3/2012 | Kenalty et al. | |
| 2012/0063487 A1 | 3/2012 | Albrecht | |
| 2012/0065478 A1 | 3/2012 | Lin et al. | |
| 2012/0109688 A1 | 5/2012 | Yoo | |
| 2012/0156933 A1 | 6/2012 | Kreger et al. | |

OTHER PUBLICATIONS

Dolan, Brian, "BodyMedia to offer disposable health tracking patch", mobihealthnews, Jan. 9, 2012, http://Mobihealthnews.com/15669/bodymedia-to-offer-disposable-health-tracking-patch/.

Zwierzchowski, Stan, "WiTAT Smart Bandage Wireless Temporal Artery Thermometer: A First Step in WVSM", University of Calgary, Canada, presented Nov. 14, 2008.

TraxIt, Children's Axillary Thermometers, http://www.medicalindicators.com/html/traxit.html, printed Feb. 22, 2012.

Exergen Temporal Scanner™, http://www.exergen.com/medical/TAT/tatconsumerpage.htm, printed Feb. 22, 2012.

CVS Remote Temperature Monitoring System, http://www.amazon.com/wireless-thermometer-remote-temperature-monitoring, printed Feb. 22, 2012.

Comstock, Jonah, "FDA clears iPhone-enabled body thermometer", Nov. 16, 2012, http://Mobihealthnews.com/19110/fda-clears-iphone-enabled-body-thermometer/.

Nosta, John, "The Thermometer Meets the Smart Phone: Technology that Help Moms and Saves Lives", Forbes, Nov. 14, 2012, http://www.forbes.com/sites/johnnosta/2012/11/14/the-thermometer-meets-the-smart-phone-technology-that-help-moms-and-saves-lives/.

Hardy, Quentin, "Big Data in Your Blood", The New York Times, Sep. 7, 2012, http://bits.blogs.nytimes.com/2012/09/07/big-data-in-your-blood/.

* cited by examiner

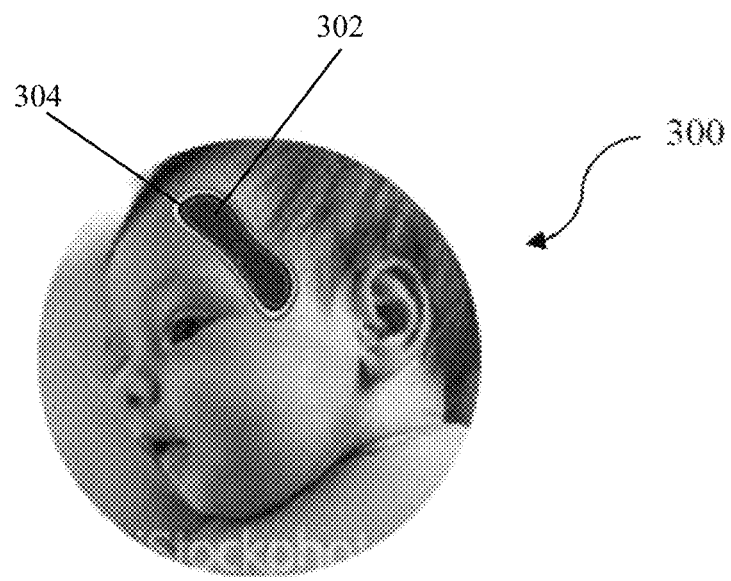
FIG. 21
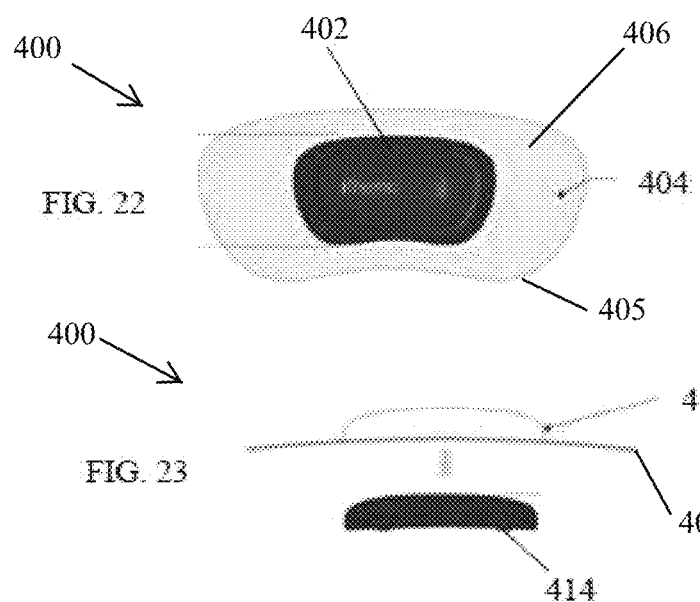
FIG. 22
FIG. 23

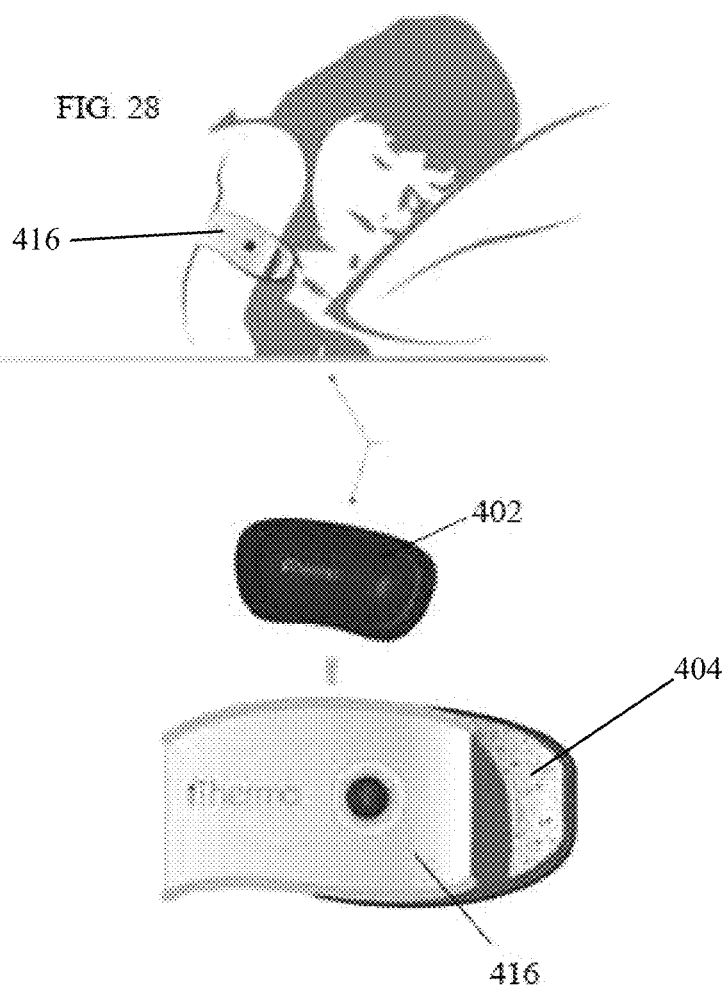

WIRELESS THERMOMETER AND METHOD OF USE THEREOF

CROSS-REFERENCE TO RELATED APPLICATIONS

This patent application is claims the benefit under 35 U.S.C. §119(e) of U.S. Provisional Patent Application Ser. No. 61/635,847 filed Apr. 19, 2012, the disclosure of which is hereby expressly incorporated by reference as part of the present disclosure as if fully set forth herein.

FIELD OF THE INVENTION

The present invention relates generally to a sensor device configured to wirelessly communicate with other electronic devices, and more specifically, a temperature sensor.

BACKGROUND OF THE INVENTION

In general, devices used to measure temperature, such as body temperature, are known. If it is determined that one's body temperature is not within the normal body temperature range, it can indicate an illness or other health condition, e.g., hypothermia. It is desirable if not necessary to continue to monitor one's temperature to determine the individual's state of health, to determine what further treatment or action to take, or whether the individual is improving or responding to treatment. In a hospital or other medical facility setting, medical personnel will typically check a patient's temperature on a pre-determined schedule In addition to consuming personnel resources, this can be disrupting to the patient, especially if the patient needs to be awaken. Even outside a medical facility setting, for young children who regularly sleep for many hours of the day and night, for example, especially when ill, measuring and monitoring their body temperature can become a great source of agitation to both the child and parents as parents, using known thermometers, must regularly disturb or wake up their child to measure the child's temperature causing both the child and parents to lose sleep.

SUMMARY OF THE INVENTION

In one embodiment, an apparatus senses body temperature and wirelessly communicates measured data to at least one electronic device. The apparatus can comprise a sensor device having a housing base, a housing cover releasably mountable to the housing base, and components for sensing body temperature and wirelessly communicating the measured data including a temperature sensor, a power supply, a microprocessor, and a transmitter and receiver.

The housing base can have a protrusion in which the temperature sensor is arranged and the protrusion can be contactable with a user to obtain a body temperature reading of the user. The housing base can also have a groove and a lip. Furthermore, the housing cover can have a projection extending therefrom and arranged in the groove to define a channel. Additionally, the apparatus can further comprise a flexible carrier, which has an aperture therein for releasably retaining, for example by press-fit, the sensor device. The sensor device can be retained by the channel in the aperture of the carrier. Alternatively or in addition to the channel, the sensor device can be retained via the lip on the carrier. The carrier, which can be breathable, can be comprised of a frame, an adhesive layer with a first side and a second side, and a backing. The first side of the adhesive layer can be affixable to the frame and the second side can be affixable to a user after removal of the backing layer.

The temperature sensor can be a thermistor or a thermocouple. The power supply can be a battery, which is disposable or rechargeable, and/or alternating current or direct current, supplied via a power cord. The apparatus can further comprise at least one light, such as an LED. The microprocessor can include embedded software and dynamic memory storage. The transmitter and the receiver can communicate with the at least one electronic device via at least one of: R-F communication, infrared communication, Bluetooth communication, and Wi-Fi communication. Moreover, the at least one electronic device can be at least one of a: smart phone, a tablet, a mobile computer, and a desktop computer.

In another embodiment, a kit comprises a sensor device that has a housing base, a housing cover releasably mountable on the housing base, and components for sensing body temperature and wirelessly communicating the measured data including a temperature sensor, a power supply, a microprocessor, and a transmitter and receiver, a carrier, which retains the sensor device, and a charging unit. The charging unit can comprise a charging cover, a charging base, a port within the charging base for fittingly receiving the device therein, and a power cord, which can be connectable to at least one of a wall outlet or a USB device. Additionally, the charging unit can include a storage unit for storing the carrier.

In yet another embodiment, a method for sensing body temperature and wirelessly communicating measured body temperature to at least one electronic device comprises the steps of connecting a device for sensing body temperature wirelessly to the at least one electronic device, attaching the device to a user, measuring the body temperature of the user, transmitting the measured body temperature of the user wirelessly from the device to the at least one electronic device, and displaying the temperature on the at least one electronic device. The temperature measured can be displayed in an application installed on the at least one electronic device. Moreover, the body temperature measured can be wirelessly transmitted from the sensing device to at least one of a: smart phone, a tablet, a mobile computer, and a desktop computer. Furthermore, the method can comprise the step of transmitting data, which can include measurement instructions, from the at least one electronic device to the device sensing body temperature.

In a further embodiment, a method of assembling a sensing device and a carrier for sensing body temperature and wirelessly communicating measured data to at least one electronic device comprises the steps of providing the sensor device, providing the carrier having an opening, and arranging the sensor device in the opening engaging the sensor device of the carrier. The sensor device can be press-fit into the carrier. Moreover, the carrier can have a perforated tab extending into the opening and the method can further comprise the step of pulling the tab to release the sensor device from the carrier.

Other objects and advantages of the present invention, and/or of the current embodiments thereof, will become more readily apparent in view of the following detailed description and the accompanying drawings.

BRIEF DESCRIPTION OF THE DRAWINGS

FIG. 11b is a schematic view of a final assembly of FIG. 11a;

FIG. 21 illustrates the temperature sensor assembly of FIG. 10 in use on a child;

FIG. 22 is a top view of another embodiment of a temperature sensor assembly, which includes a sensor device and a carrier;

FIG. 23 is a schematic view of the assembly of the temperature sensor assembly of FIG. 22;

FIG. 27 is an assembly view of an embodiment of a temperature sensor and an armband assembly, which can be used to secure the sensor to a user's arm;

FIG. 28 illustrates the assembly of FIG. 27 in use on a person;

DETAILED DESCRIPTION OF EMBODIMENTS OF THE INVENTION

Figure 1:
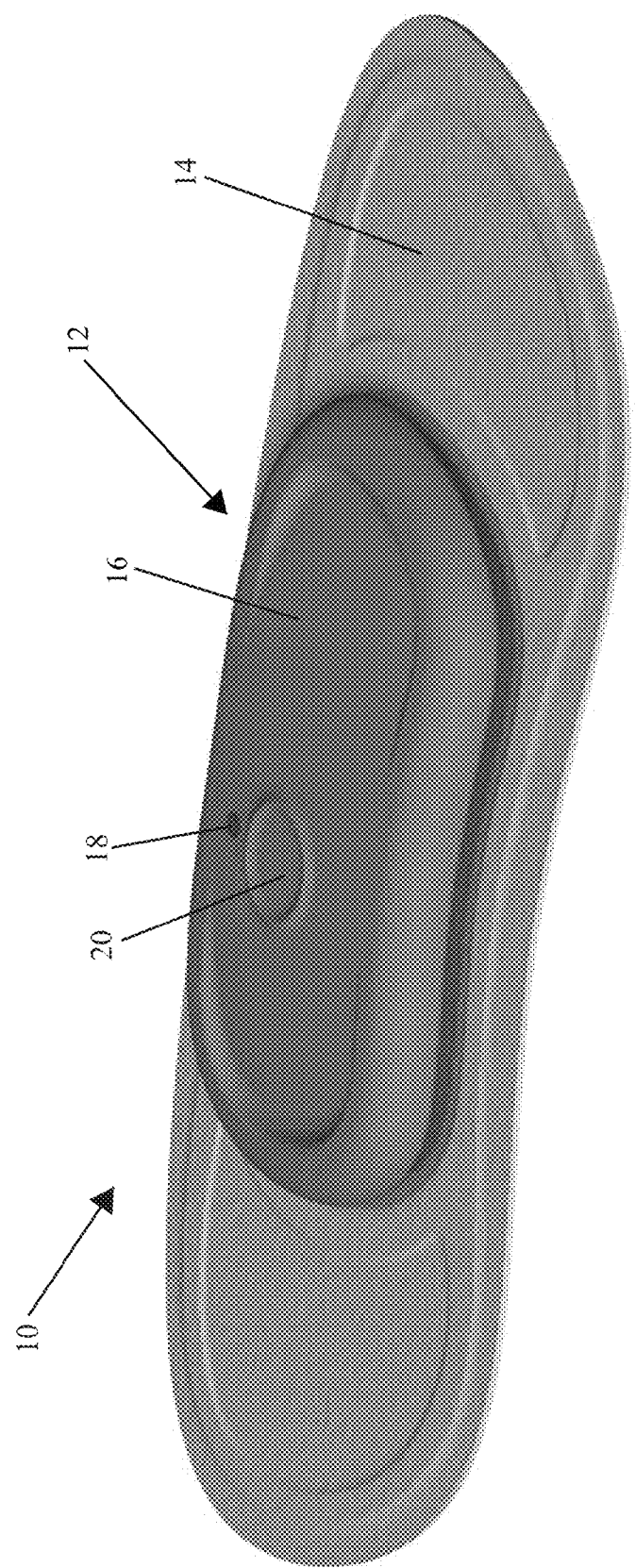
FIG. 1 is a perspective top view of an embodiment of a temperature sensor assembly, which includes a sensor device and a carrier.
Figure 2:
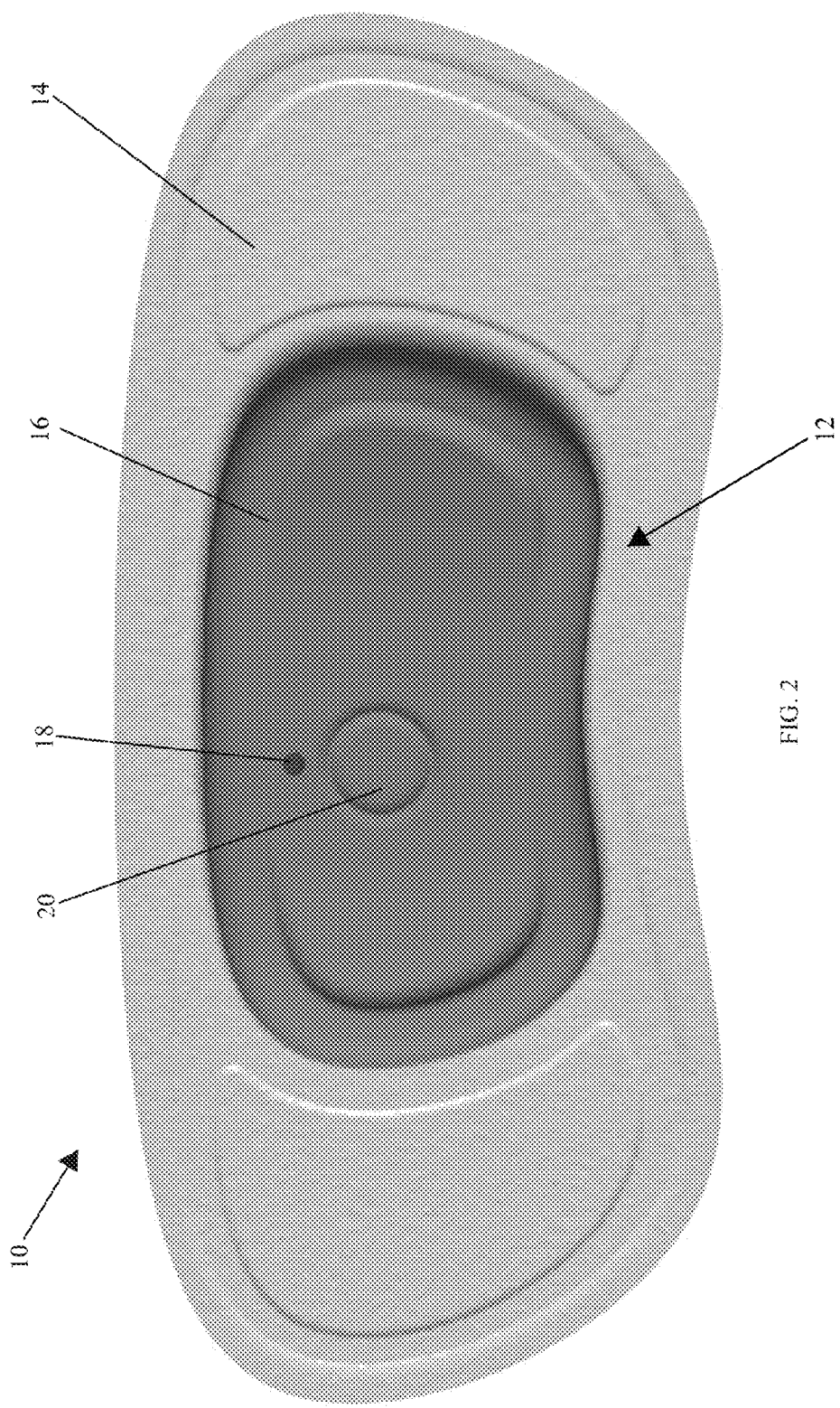
FIG. 2 is a top view of the temperature sensor assembly of FIG. 1.
Figure 3:
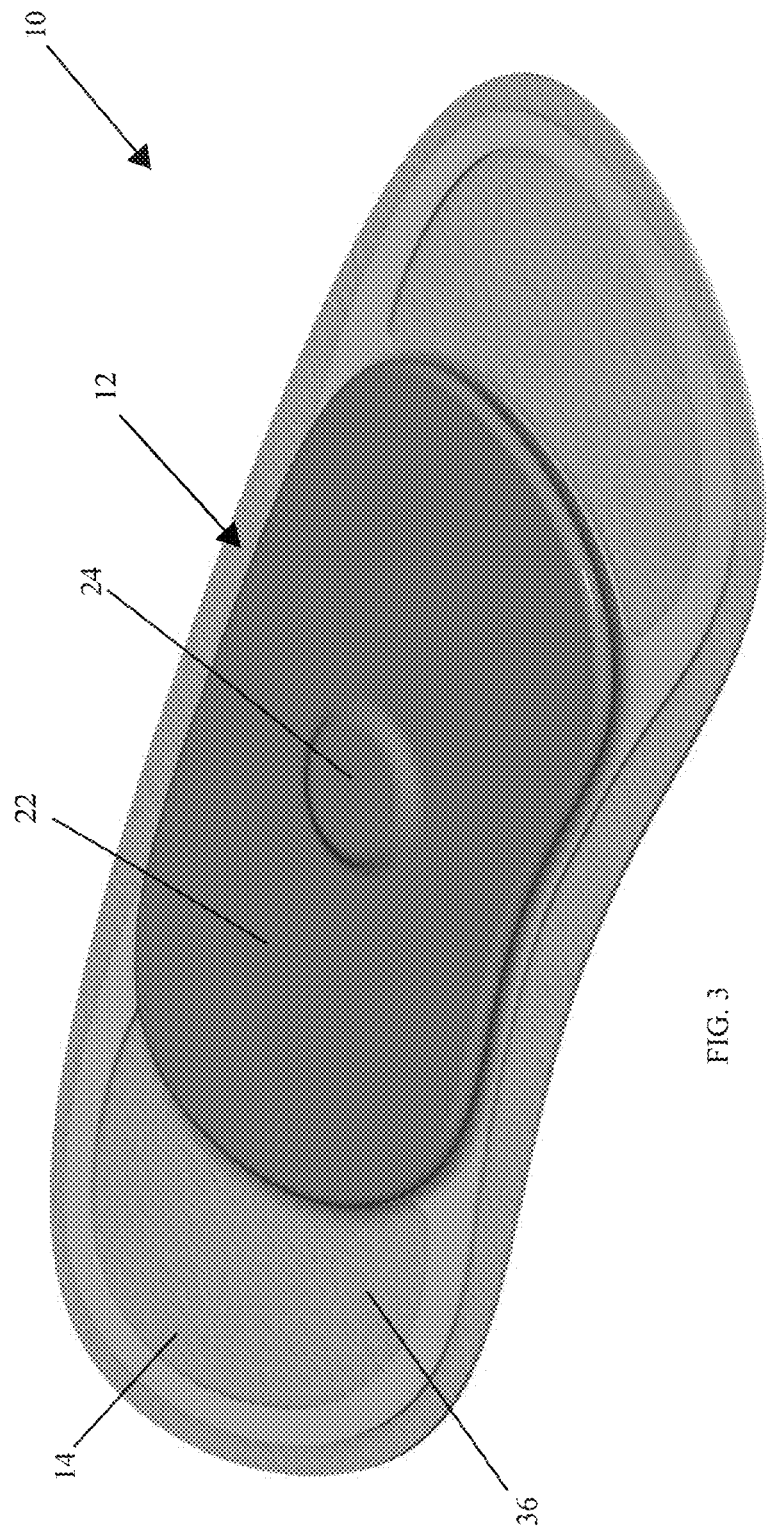
FIG. 3 is a perspective bottom view of the temperature sensor assembly of FIG. 1.

FIGS. 1 through 6 illustrate an embodiment of a wireless thermometer assembly that is indicated generally by reference numeral 10. Broadly, the thermometer assembly 10 includes a sensor device 12 and a flexible carrier 14 engageable to the sensor device 12, as described below. As depicted in FIGS. 1 and 2, the sensor device 12 comprises a housing cover 16 that defines an aperture 18 for viewing of an LED indication of various states of the device 12 (described below) and an contoured portion forming an indented power button 20. As shown in FIG. 3, the sensor device 12 also comprises a housing base 22, which includes a projection 24 that can be placed against a user's skin to obtain a temperature reading, as described below.

Figure 4:
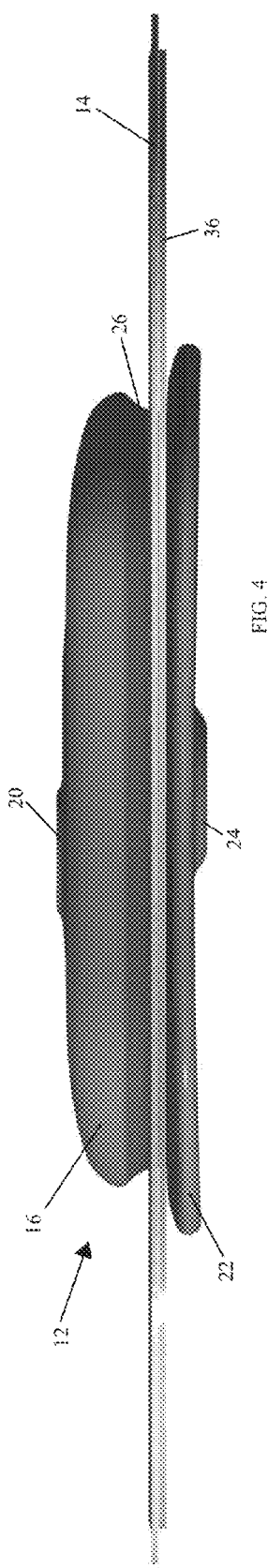
FIG. 4 is a side view of the temperature sensor assembly of FIG. 1.
Figure 5:
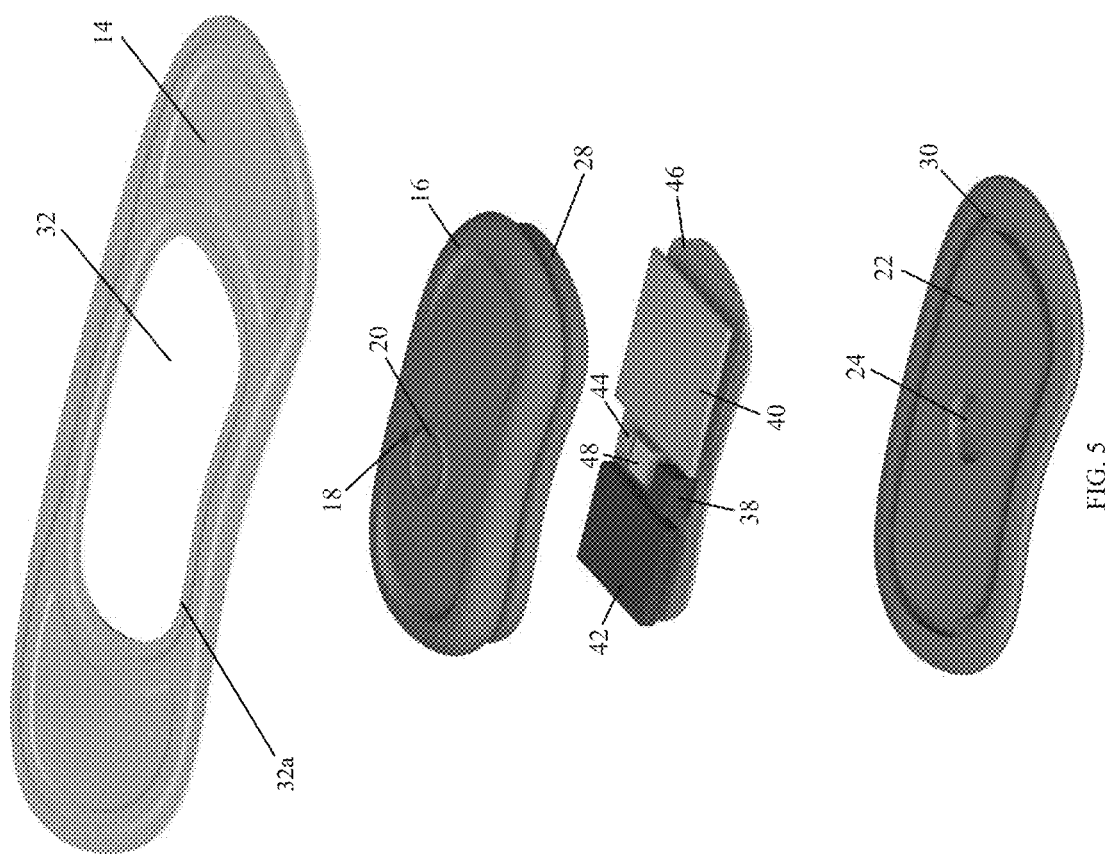
FIG. 5 is an exploded view of the temperature sensor assembly of FIG. 1.

In an assembled state, as shown in FIG. 4, the housing cover 16 is attachable to the housing base 22 to enclose the components of the sensor device 12 located therebetween the housing cover 16 and the housing base 22. When assembled together, the housing base 22 and housing cover 16 define a peripheral channel 26 therebetween as shown in FIG. 4. As depicted in FIG. 5, the housing cover 16 includes an peripheral projection 28 that extends therefrom, and the housing base 22 has a groove 30 in which the peripheral projection 28 fittingly engages to define the peripheral channel 26. In combination, the housing cover 16 and housing base 22 define a thickness of the assembled sensor device 12 (e.g., 3 mm to about 6 mm). In some embodiments, the housing cover 16 and housing base 22 are permanently attached to each other, e.g., by adhesive, welding, etc. Alternatively, the housing cover 16 and housing base 22 may be releasably attachable, e.g., a friction fit, in order to access the internal components of the sensor 12, e.g., for service or replacement.

As shown in FIG. 5, the carrier 14, which can include a surface that adheres to a user's skin, e.g., adhesive layer 36 an underside of the carrier 15, has an opening 32 therein, the periphery 32a of which generally corresponds to the shape of the peripheral channel 26. To releasably retain the sensor device 12 in the carrier 14, the carrier 14 is moved over the housing cover 16 until it is received in the peripheral channel 26, the sensor 12 engaged within the opening 32 (See FIG. 4). As seen in FIG. 4, the housing cover 16 is larger than the opening 32, and thus interferes with the periphery 32a upon installation of the carrier 14. To install the carrier 14, a force is applied to the carrier 14 relative to the housing cover 16 (downward in FIG. 4), deflecting the periphery 32a so as to elastically deform the opening 32 to the size of the housing cover 16, allowing it to pass over the housing cover 16 and into the peripheral channel 26. Once the carrier 14 passes by the enlarged portion of the housing cover 16, the carrier 14 elastically returns to or nearly to its original shape, e.g., smaller than the housing cover 16. In such manner, the carrier 14 can be retained in the peripheral channel 26.

Conversely, to separate the carrier 14 from the peripheral channel 26, an opposite force is applied to the carrier 14 relative to the housing cover 16 (upward in FIG. 4), to deform the carrier 14 and opening 32 to be able to move the carrier 14 over and past the housing cover 16. As should be understood by those of ordinary skill in the art, the carrier 14 can be made of a material and have a configuration that permits it to be sufficiently flexed to install it over the housing cover 16, e.g., plastic, silicone, rubber, metal, etc. The modulus of flexibility of the carrier 14, e.g., as determined by the material and configuration, and/or the degree of interference between the carrier 14 and the housing cover 16, can be selected to permit assembly of the carrier 14 and sensor 12 without excessive force (making it difficult for a user to install/disassemble). At the same time, these characteristics can be selected so that sufficient force is necessary to mitigate accidental or unintentional disassembly of the carrier 14 and sensor 12.

In some embodiments, the carrier 14 can define a length within the range of about 1.50 inches to about 1.80 inches, and can be within the range of about 1.60 inches to about 1.70 inches. Also, in some such embodiments, the carrier 14 can define a width within the range of about 0.08 inch to about 1.2 inches and can be within the range of about 0.09 inch to about 1.10 inches. In some embodiments the carrier 14 may be reusable. In other embodiments the carrier may be disposable. Although various embodiments are described herein, it should be recognized that the carrier 14 can be of any desired length, width, and shape that can accommodate the sensor device 12. However, as may be recognized by one of ordinary skill in the pertinent art based on the teachings herein, the sensor device may be placed on a user via any of numerous releasable attachment methods, currently known, or that later become known.

Figure 6:
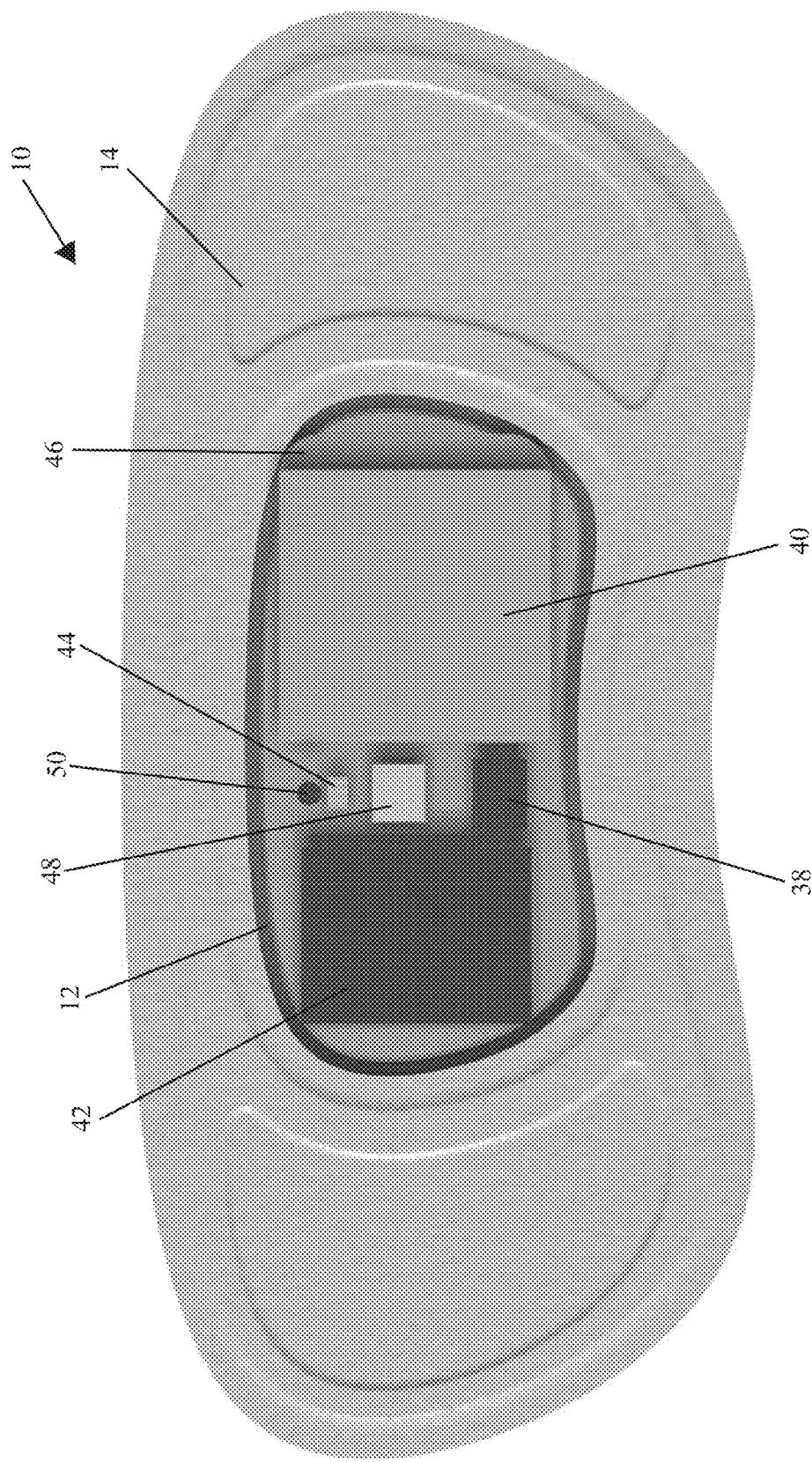
FIG. 6 is top view of the temperature sensor assembly of FIG. 1 with a housing cover removed to show internal components of the sensor device.

As shown in FIGS. 5 and 6, various components are housed between the housing cover 16 and the base 18 of the sensor 12. These components can include a temperature sensor 38, such as, for example, a thermistor or thermocouple, a power supply 40, a microprocessor 42 with embedded software and dynamic memory, a radio transmitter 44 and a receiver 46 with an antenna, a power switch 48, and one or more light emitting diodes (LED) 50, or alternatively, a multi-color LED. The antenna may consist of PCB antenna, or chip antenna, or integrated antenna in the radio IC/module. However, as may be recognized by one of ordinary skill in the pertinent art based on the teachings herein, any of numerous other internal components currently known, or that later become known, necessary for the integration and proper functioning of the aforementioned internal components may be included within the thermometer housing.

In some embodiments, the power supply 40 may be in the form of a rechargeable battery or batteries that may provide power for approximately 24 hours on a single charge. In other embodiments, the power supply 40 may be in the form of a disposable/replaceable battery or batteries. In yet other embodiments, the sensor device 12 may receive external AC or DC power via a power cord connectable in electrical communication with the sensor 12 in a known manner. In embodiments where the sensor device 12 is powered via rechargeable batteries that can be fully charged, for example, in approximately 1 hour, the thermometer assembly 10 may further include a plug (not shown) for connecting to an external power source and/or a charging antenna (not shown) for capturing energy from a charging system.

The LED(s) 50 indicate various states of the device through the aperture 32 of the housing cover 12. Various states of the device may include ON, OFF, searching for wireless connection, connected, low battery, charging, and/or fully charged. However, as may be recognized by one of ordinary skill in the pertinent art based on the teachings herein, any of numerous states of the device, currently known, or that later become known, may also be indicated. In some embodiments, the LED(s) may indicate various states of the device via different colors. In some embodiments, the LED(s) may indicate various states of the device via a constant light and/or different blinking light patterns. In yet other embodiments, the LED(s) may indicate various states of the device via a combination of color and blinking patterns. In other embodiments, the LED (s) may indicate various states utilizing different light intensities (brightnesses), alone or in combination with colors and solid/blinking patterns. However, as may be recognized by one of ordinary skill in the pertinent art based on the teachings herein, any of numerous other light sources currently known, or that later become known, may be utilized to perform the function of indicating various states of a device.

Figure 7A:
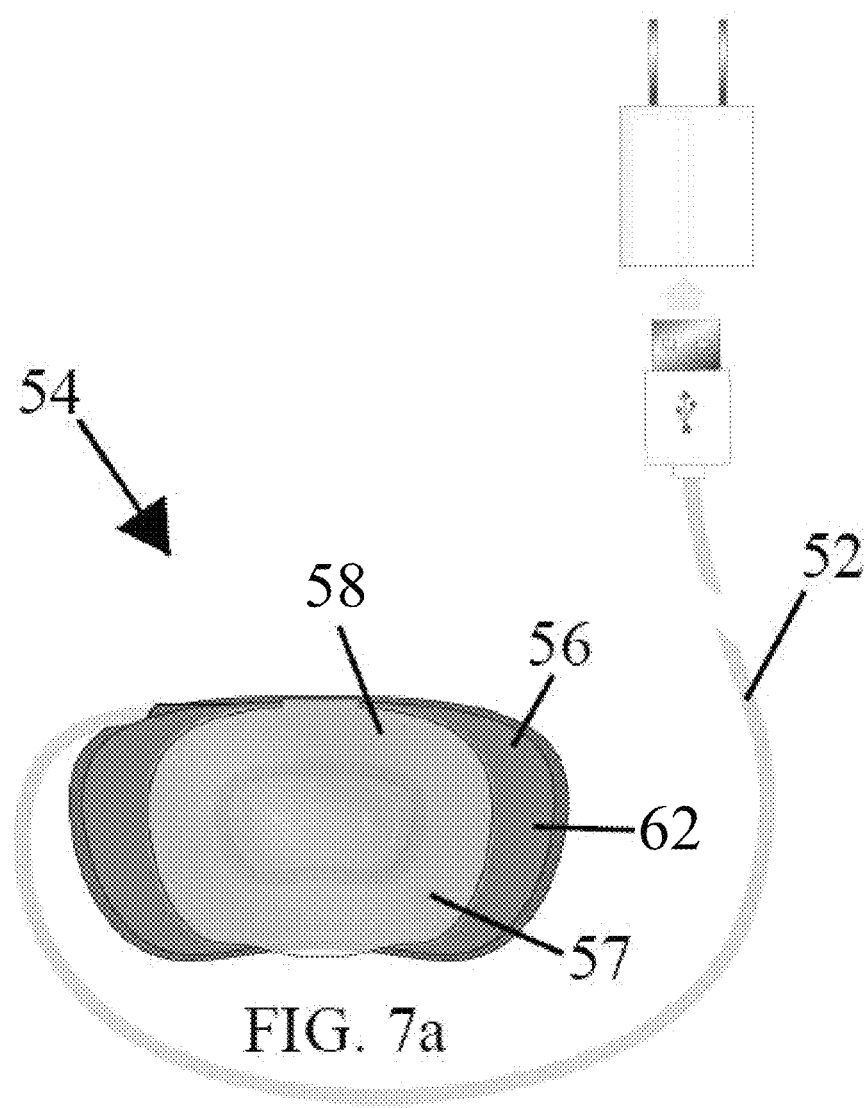
FIGS. 7a-7e show an embodiment of a charger unit for use with temperature sensor assembly of FIG. 1.
Figure 7B:
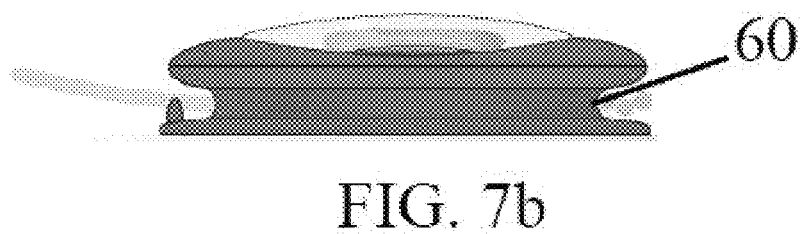
Figure 7C:
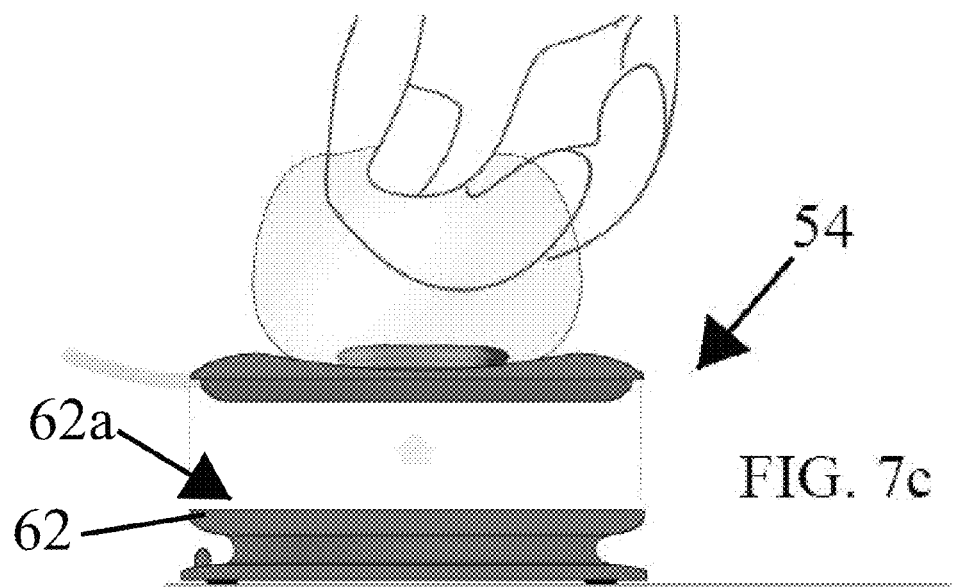
Figure 7D:
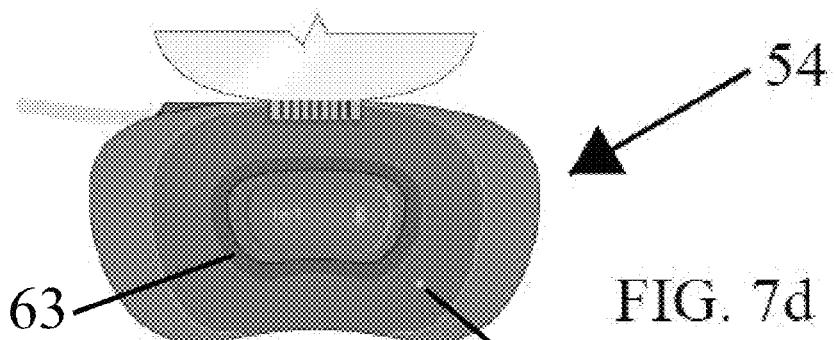
Figure 7E:
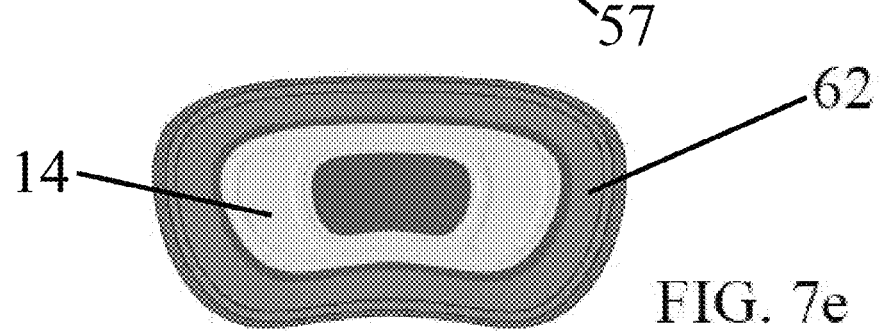

FIGS. 7a-7e illustrate an embodiment of a charging system 54 for charging the sensor device 12, in embodiments where the power supply 40 includes a chargeable/rechargeable power supply, e.g. rechargeable batteries. More specifically, FIG. 7a depicts a top view of the charging system 54. The charging system 54 includes a charger base 56 to which is hingedly attached a charger cover 58, and a storage unit 62. Alternatively, the charger cover 58 can be removably attachable to the charger base 56 by other mechanisms, e.g., friction fit, snap fit, etc., as should be understood by those of ordinary skill in the art. The charger base 56 includes a power cord 52 protruding therefrom for attachment to a power source. As may be recognized by one of ordinary skill in the pertinent art based on the teachings herein, the power cord 52 may be configured and connectable to any of numerous power sources, currently known, or that later become known, such as, for example, a wall outlet, a transformer (such as a DC transformer), or a USB outlet. The charger base 56 may also include a notification light 57, e.g., one or more LEDs, indicating via different colors, intensities and/or different blinking patterns the status of the sensor device 12, e.g., whether the sensor device is discharged, charging or fully charged. The charger cover can be transparent or translucent to allow the status of the sensor device to be viewed while the cover is in the closed position. The charging system 54 can also include a storage unit 62 defining an interior storage space 62a for storing one or more adhesive carriers 14 therein. As seen best in FIG. 7b, which is a side view of the charging system 54 and FIG. 7c, which shows separation of the charging base 54 from the storage unit 62, the charger base 56 and storage unit 62 are substantially complementary configured so that the charger base 56 and storage unit can be removably assembled. In this manner, the interior storage space 62a can be enclosed, as seen in FIG. 7b. In the illustrated embodiment, the storage unit 62 includes a peripheral channel 60 in the sidewall of the storage unit 62, which can be used to wrapping wrap the cord 52 around the storage unit 62 when not in use. FIG. 7d illustrates a top view of the charger base 56 with the charger cover 58 in an open position. The charger base 56 defines a port 63 to fittingly receive the sensor device 12 for recharging thereof. Finally, FIG. 7e illustrates a top view of the storage unit 62 with a carrier 14 stored therein.

As may be recognized by one of ordinary skill in the pertinent art based on the teachings herein, the thermometer may utilize any of numerous different charging units currently known, or that later become known, for charging thereof. In some embodiments, the sensor unit 12 has an electrical contact in electrical communication with the power supply 40, and the port includes an electrical contact in electrical communication with power cord 52. The electrical contacts of the sensor unit 12 and port are positioned relative to each other such that, when the charger base 56 is engaged with the port, the electrical contacts of the sensor and port are placed into electrical contact with each other. Power provided to port via the power cord 52 can then transfer to the sensor and charge/recharge the power supply 40 of the sensor unit 12.

In other embodiments, for example, a charging system can be employed to ensure operability of the sensor device 16 providing wireless charging through the use of an inductive coupling of electrical energy from a charging source that is housed within the port 63, which in such embodiments defines an external charging cradle (holder). The charging cradle can include an inductive coupling device that has a wire coil with or without a magnetic core or core material. The charging cradle is electrically connectable to the power cord 52. To charge the sensor 16, the sensor 16 can be placed into the cradle of the charging system 54. An alternating current (AC) signal can be applied to the wire coil (e.g., from a wall outlet) in order to produce a field that will be applied to a receiving coil (not shown) housed within the sensor. The sensor 16 may include electronics that regulate the received recharge energy as it is applied to the battery or batteries. The charging source may operate continuously, may only provide power to the inductive charging source when the sensor 16 is detected to be in the charging cradle, or when a cover 58 or other retention mechanism is in place. In another embodiment, the charging cradle can provide a constant inductive charging field without any communication or power level adjustment regardless of the state of charge present within the battery or batteries 40 of the sensor 16. In a further embodiment, the charging cradle may also be able to regulate the charging field based on communication between the sensor and the charging cradle as described below. For example, the charging cradle can contain electrical controls adapted to alter the frequency and/or voltage and/or the current applied to the inductive element in the charging cradle depending on information provided regarding the state of charge, temperature, or condition of the battery or batteries 40 housed within the sensor 16 or the functional status of the sensor 16.

In some embodiments, the sensor device 16 is capable of monitoring and regulating the state of the charge of a rechargeable battery or batteries using an overcharge regulation system or an over-discharge protection system.

Using an overcharge regulation system, externally supplied charging energy can be regulated internally by the sensor device 16 to prevent an overcharge of the battery or batteries 40, which will prevent battery system damage. The overcharge regulation system can employ various mechanisms including, but not limited to: (1) over-voltage protection, where peak voltage of the battery is limited or "clamped" to prevent additional charge energy from being applied to the battery 40; (2) temperature protection, where the temperature of the battery and/or the ambient environment may be monitored to reduce or prevent charging from occurring when temperatures exceed predetermined temperature specifications for property battery operation; or (3) an integrated charge tally ("Coulomb Counting") where the current that is supplied to the battery 40 is measured.

Using the integrated charge tally mechanism, the amount of charge applied to the battery 40 during charging is measured by integrating the measured charge current over the time period that the charge is applied (charge=current+time). The applied charge can be added to a known starting state of charge (Amp-hours) to determine the charge state (in Amp-hours) of the battery 40. As is known, the starting charge can, for example, be stored in a memory, which can be non-volatile, in the sensor 16. Prior to any charge, the state of charge is presumed zero, and the charge state is determined going forward on a cumulative basis (charge and discharge) When the sum of the measured integrated charge current-time product and the starting Amp-hour state of charge reach a maximum value, e.g., full battery charge, the recharge energy may be gradually reduced or the recharge can be terminated.

Alternatively, using an over-discharge protection system, the sensor device will stop functioning and prevent a further drain and ultimately damage to the battery or batteries. Over-discharge protection can be activated when certain criteria is met that indicates that the battery or batteries is fully depleted or has encountered other conditions that require battery discharge to terminate. When over-discharge protection is activated, warnings indicating a low battery condition could be sent to the user or other connected devices, which indicate that a cutoff is imminent. A low battery condition and, thus, an under-voltage condition might be met where the battery voltage drops below or equals a set voltage level indicating that the battery is fully depleted. Additionally, an indication that a battery or batteries may be nearing depletion could be met by measuring the integrated charge tally, which is determined by integrating the current over the time of the discharge or usage period. Moreover, increasing temperature can be used to indicate that the battery is nearing a depleted state. Furthermore, increasing internal resistance can additionally be used to indicate that the battery is nearing a depleted state.

In other embodiments, the state of charge of a battery or batteries within a sensor device can be provided using one or more techniques, which include: (1) integrated charge tally; (2) open circuit voltage; and (3) over-discharge protection, in combination. The integrated charge tally technique, where the current that is supplied to the battery or batteries is measured, has been discussed above. However, it should be noted that the capacity of the battery or batteries may change over time due to degradation that is typically associated with battery life. The available Amp-hour capacity of the battery or batteries may be reduced, requiring that the state of charge measurement be adjusted to reduce the point at which the battery or batteries is considered to be fully charged. This may be accomplished by comparing the amount of current that was drawn from the battery or batteries during operation to the amount of battery capacity supplied during recharge. An algorithm would be employed to determine if the battery or batteries capacity has been reduced and would then adjust the maximum capacity used for state-of-charge.

For the open-source voltage technique, using a low power microcontroller and associated measurement circuitry, the voltage of the battery or batteries 40 may be measured and compared to a lookup table or mathematical function, which may be stored in memory of the sensor 16 or even the charging system 54, that will relate the open circuit, or lightly loaded battery voltage to the state of charge, since the state of charge of a battery or batteries is often correlated to the measured open circuit voltage. Temperature may be used as a factor in the determination, since in many battery systems, the voltage apparent on the terminals may be significantly affected by the temperature of the battery. A lookup table relating the voltage at various stages of charge to the battery or batteries 40 of temperature may be included in the sensor 16.

Using the discharge rate dependent capacity measurement technique, a high discharge slope may be obtained by applying a known discharge current to a battery or batteries. This may be due to factors such as dynamic internal impedance and diffusion rates of the electrolyte and active materials. As a battery or batteries become increasingly depleted, the internal impedance generally increases. This has the effect of creating a lower VUL (voltage under load). By evaluating the increasing internal resistance, this can be correlated to state of charge. Additionally, as the battery active materials react during a discharge, the diffusion rate of electrolytes or reaction rates of the active materials tend to decrease, which has the apparent effect of increasing slope of the VUL. This change in voltage can be expressed as a change in voltage over time, or dV/dt ratio. This value can additionally be used to determine the remaining available capacity by applying a known constant current load, or by measuring the current load as the device is operating over a fixed period of time. The dV/dt ratio can then be calculated and compared to a look up table or other function that will correlate the dV/dt ratio to the state of charge. In another embodiment, battery impedance can be measured and utilized as an indication of a battery condition. Battery impedance can be measured using various methods. One method could be to perform a dV/dI measurement. In this method, a battery is subjected to two short duration constant current discharge pulses. The duration of the pulses can be less than 100 ms, but longer than 10 ms depending on the electrochemistry of the battery being measured, as should be understood by those of ordinary skill in the art. The duration of the pulses should be equal. The first pulse is generally a low current pulse and is applied at a rate that is at least 10 times less than the peak expected current drain from the battery in the application. The second pulse is applied at a rate that is at least 10 times greater than the discharge current of the first low current pulse. Each pulse will require the measurement of the battery voltage just prior to the end of the pulse. The measured voltage on each pulse will be a measured VUL. The internal resistance of the battery is determined by the following equation:

$$R_b = \frac{(V_{p1} - V_{p10})}{(I_{p10} - I_{p1})}$$

Once measured, the internal impedance can be used to aid in the determination of the state of charge during discharge or recharge functions. Increasing internal resistance can be used to indicate that the battery is nearing end of life.

In yet other embodiments, the transmission of the state of charge or general battery condition may be provided using several indication methods. In one such embodiment, a light or lights, such as an LED or LEDs, which are mounted on or within the sensor device, can be used to indicate state of charge. Various states of the device may include ON, OFF, searching for wireless connection, connected, low battery, charging, and/or fully charged. However, as may be recognized by one of ordinary skill in the pertinent art based on the teachings herein, any of numerous states of the device, currently known, or that later become known, may also be indicated. In some embodiments, the light or lights may indicate various states of the device via different colors. In other embodiments, the light or lights may indicate various states of the device via a constant light and/or different blinking light patterns. In yet other embodiments, the light or lights may indicate various states of the device via a combination of intensity, color and blinking patterns. In other embodiments, lights can also be used to indicate battery conditions such as over-temperature, high impedance or end of life. However, as may be recognized by one of ordinary skill in the pertinent art based on the teachings herein, any of numerous other light sources currently known, or that later become known, may be utilized to perform the function of indicating various states of a device. In yet another embodiment, RF or wireless communication indicating the state of charge or other battery conditions such as internal impedance, temperature or capacity can be achieved using the radio communications capability within the sensor to an information display device such as a phone, computer or tablet that has a radio or wireless receiver. The display device can include an application or program that is programmed to receive and process the transmitted information and display or otherwise communicate this information regarding battery status to the user. Additionally, in another embodiment, RF or other communication indicating the state of charge (gas gauge) or other battery conditions such as internal impedance, temperature or capacity can be achieved between a sensor device and a charging cradle. The cradle can utilize this information to adjust the parameters that control the charging power supplied to the sensor device. Additionally, indicators on the charging station, such as lights, LEDs, etc., via, for example, an intensity, color change, blinking patterns, audible transducers, or displays can be used to indicate the state of charge of the battery, charging state (charge, charge completed, error, etc.) or battery condition to the user.

Figure 8:
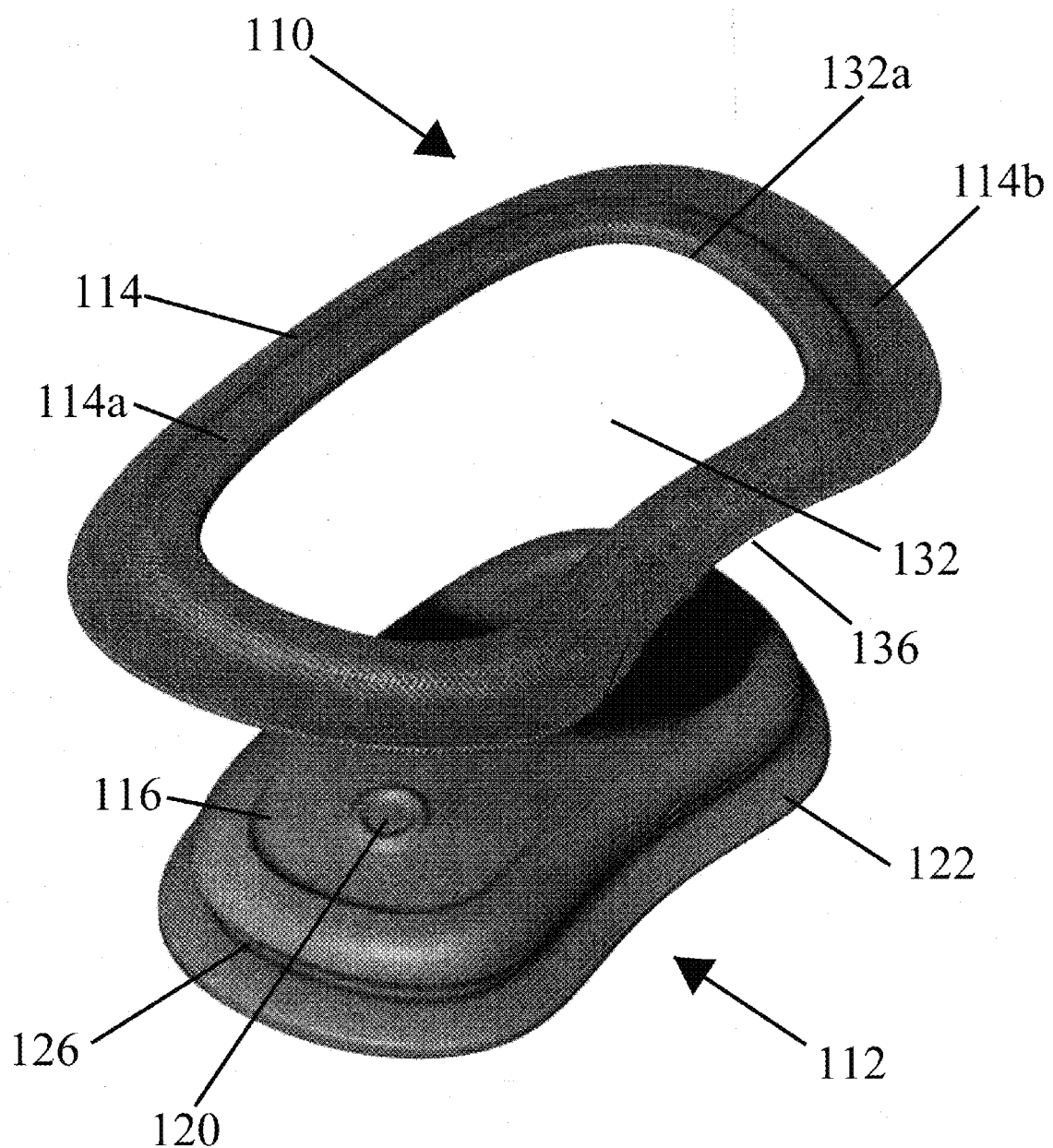
FIG. 8 is a perspective view of another embodiment of a temperature sensor assembly showing a sensor device and a carrier prior to attachment of the components.

FIG. 8 illustrates an embodiment of a thermometer assembly 110, which includes a sensor device 112 and a carrier 114. The thermometer assembly 110 is similar to assembly 10 described above, and like or similar parts are indicated using like numbers preceded by the number "1." One difference between the assembly 10 and the assembly 110 is the carrier 114. The carrier 114 has a raised surface 114a that engages with the peripheral channel 126, and a sloping contour to aid in securing the carrier 114 to the sensor device 102 while allowing a housing cover 116 of the sensor device 112 to protrude through an opening 132 in the carrier 114. The sloping contour extends outwardly to a flange 114b. The bottom surface of the flange 114b can include an adhesive surface 136 to adhere the carrier 114, and thus the sensor unit 112, to a user's body for temperature measurement. However, carrier 114 can also include any other known tactile surfaces that would allow the carrier 114 to adhere to a user's body. The configuration of the carrier 114 places the adhesive-containing bottom surface of the flange 114b substantially flush with the skin-contacting bottom edge of the sensor unit 112. This aids in establishing and maintaining securing contact of the carrier 114 and sensor unit 112 to the skin.

Figure 9:
FIG. 9 shows the temperature sensor assembly of FIG. 8 wirelessly connected to an embodiment of an electronic device having an application installed thereon for displaying data transmitted from the sensor device.

As shown in an embodiment in FIG. 9, the thermometer assembly 100 can be wirelessly connectable to, e.g., placed into communication with, an electronic device 200 or multiple electronic devices for sending and receiving of data to be displayed in digital, analog, and/or graphical format. In the illustrated embodiment, the electronic device 200 is a smart phone. However, as may be recognized by one of ordinary skill in the pertinent art based on the teachings herein, the electronic device may be any of numerous electronic devices currently known, or that later become known, such as, for example, a tablet, a mobile computer, a desktop computer, or other wireless devices. Data transmission may be achieved via any standard format, including, but not limited to, R-F, Infrared, Wi-Fi, and Bluetooth connections. In some embodiments, the thermometer assembly may be connected to an electronic device(s) from up to 200 feet away. Also, in some embodiments, thermometer assembly may connect directly to the electronic device(s) and/or may connect indirectly to the electronic device(s) via, for example, a router, server or network. In some embodiments, the assembly may communicate with the electronic device(s) 200 via a wired connected, e.g., a USB or other data-carrying cable.

In other embodiments, the data transmitted from the thermometer assembly 100 to the electronic device(s) can include user body temperature, device identification, and device status, such as, for example, low battery, charging, fully charged and/or powered ON or OFF, lost contact with a user's skin, and loss of contact between the electronic device and the thermometer assembly. The thermometer assembly 100 may also receive data from the electronic device(s) 200 such as, but not limited to, transmission confirmation and programming instructions. Programming instructions may include, but are not limited to, instructions to sense and transmit the present temperature (instant temperature read), which allows the user to obtain the current temperature. Other programming instructions include temperature tracking for a specified period of time at specified time intervals. In some embodiments, in the instance where the thermometer assembly 100 detects a loss of connection with the electronic device(s) 200, the sensor device can continue to implement the programming instructions and store data in dynamic memory until reconnection is obtained, at which time the stored data is transmitted to the electronic device(s) 200. Although the electronic device 200 is illustrated herein with one embodiment of the thermometer assembly 100, it should be understood that the electronic device 200 can be used in conjunction with any of temperature sensors disclosed herein.

In some embodiments, the electronic device(s) may include an installed application or program that communicates with the thermometer assembly and provides a user interface, as shown in FIG. 9. The application may include multiple device support, wherein multiple sensor units can be connected, either separately or at the same time, and each paired thermometer has its own data set in the form of a profile. The user may add information to each profile, such as user name, date of birth and a picture. Within any selected profile, the application may display, the profile information as well as current body temperature and/or temperature history, as shown in FIG. 9. Temperature history may be displayed in the form of a graph and/or a chart. The application may also include notifications, such as, for example, connection notifications, battery notifications, as well as notifications to administer medications at specific times with the required dosage. Additionally the application may also include alarms in connection with the notifications. The application may include alarms in connection with sensed temperature that is out of the normal body temperature range, or surpasses a set threshold, which can include exceeding a temperature, indicating a rising fever, or falling below a temperature, indicating a reducing fever. The former can alert a user to a change in health condition or that additional treatment, e.g., a next medicine dose, is required. The latter can be useful, for example, to notify a user that a treatment has taken effect. The alarms and/or notifications may take various forms, including any of or combinations of visual (screen display, color change, blinking patterns, etc.) and audio notifications (sound, voice, etc.). Data transmitted to the application can also be exportable from the application. For example, the data may be exported from the application to a doctor's office or an insurance company. While the user uses the electronic device(s), the application may run in the background.

Figure 10:
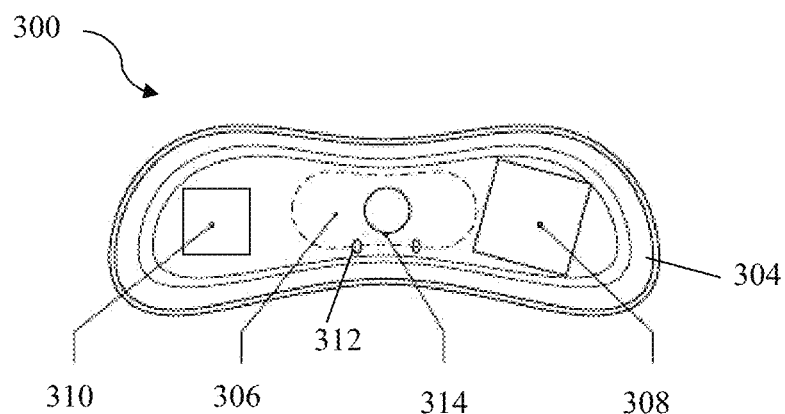
FIG. 10 is a schematic top view of another embodiment of a temperature sensor assembly, which includes a sensor device and a carrier.

FIG. 10 schematically illustrates another embodiment of a temperature sensor assembly 300, which, similarly to assemblies 10, 110 includes a sensor device 302 and a carrier 304. As shown in FIG. 10, the sensor device 302 includes a temperature sensor 306, such as a thermistor array or a thermocouple, a power supply 308, such as a rechargeable or disposable batterie(s) or external DC or AC power via a power cord, a recharging area 310, a display 312, such as LEDs, to, e.g., indicate the various states of the device 302, a power button 314 and other electronic components, which are used to integrate and allow the temperature sensor 306, power supply 308 and display 312 to function. The recharging area 310 receives power from the charging system and routes that power to the battery for recharging. The recharging area 310 can, for example, contain the components described above (hardware, software, memory, circuits, etc.) for charging the power system 104, e.g., by electric contact or inductive charging. The display 312 can be used to indicate the various states of the sensor device 302. These states can include, but are not limited to, whether the device 302 is on or off, if the device 302 is searching for a wireless signal or connected to a wireless signal, has a low battery, is charging or is fully charged.

Figure 11A:
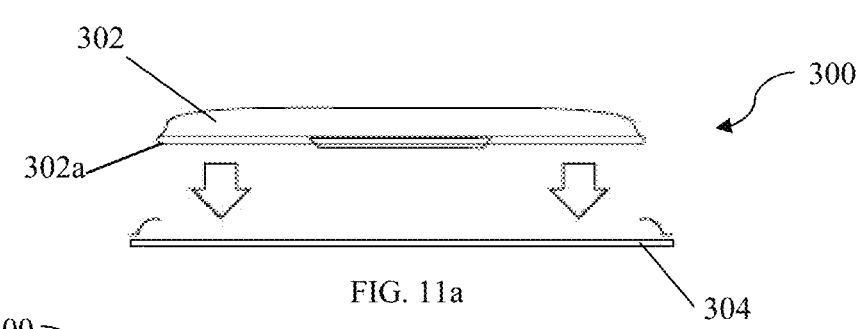
FIG. 11a is a schematic view of the assembly of the temperature sensor assembly of FIG. 10.
Figure 11B:
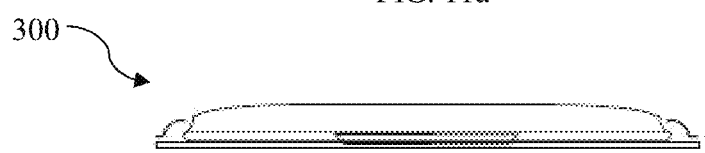

FIG. 11a schematically depicts assembly of the sensor device 302 and the carrier 304. The sensor device 302 can be connected to the carrier 304, for example, by press-fit or snap-fit, as further described below. However, any other known method of connection can also be utilized to connect the sensor device 302 to the carrier 304. In at least some embodiments, the connection ensures that the sensor device 302 and the carrier 304 will not be inadvertently separated from each other, e.g., without an intentional movement or application of force by a user. FIG. 11b schematically illustrates the sensor device 302 and the carrier 304 in a final assembled arrangement.

Figure 12:
FIG. 12 is a top view of another embodiment of a sensor device, which can be included in the assembly of FIG. 10.
Figure 13:
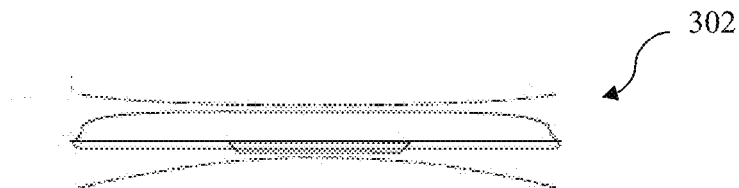
FIG. 13 is a side view of the sensor device of FIG. 12.
Figure 14A:
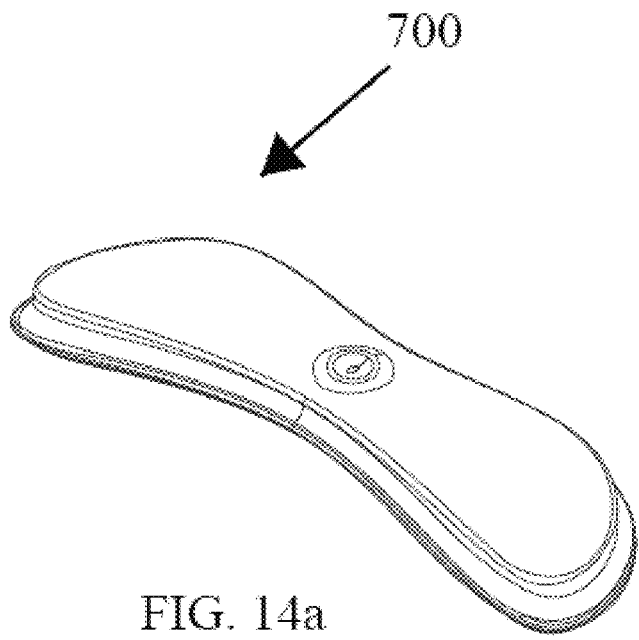
FIGS. 14a-14g respectively show a front perspective, top, front, back, bottom, left and right view of another embodiment of a sensor device, having an initially curved state.
Figure 14B:
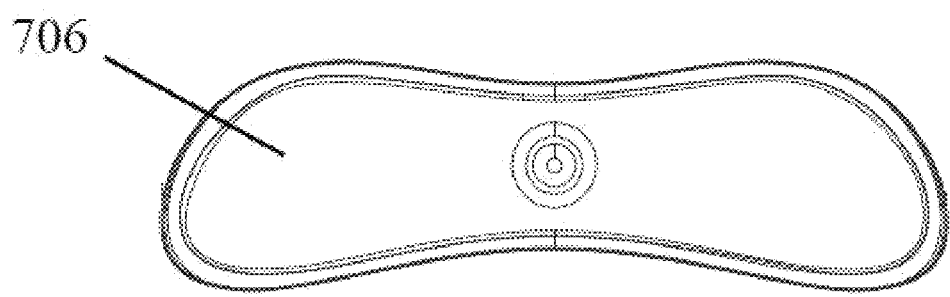
Figure 14C:
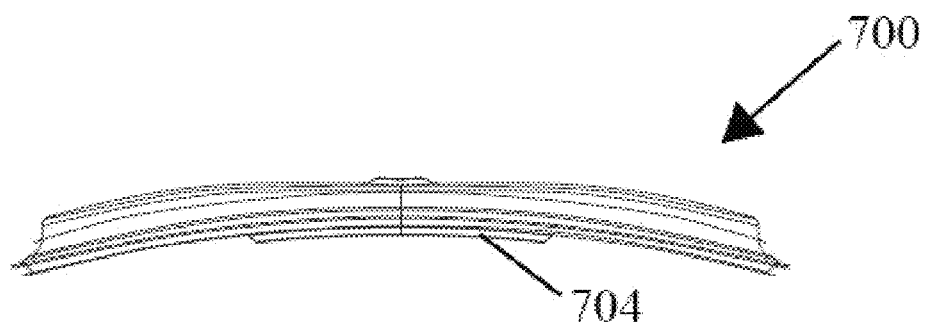
Figure 14D:
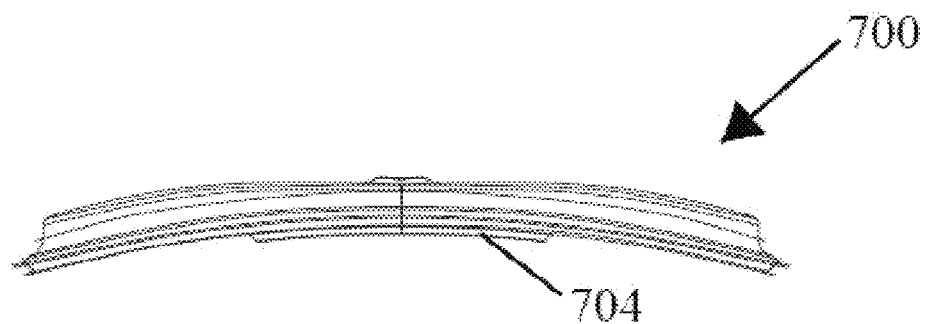
Figure 14E:
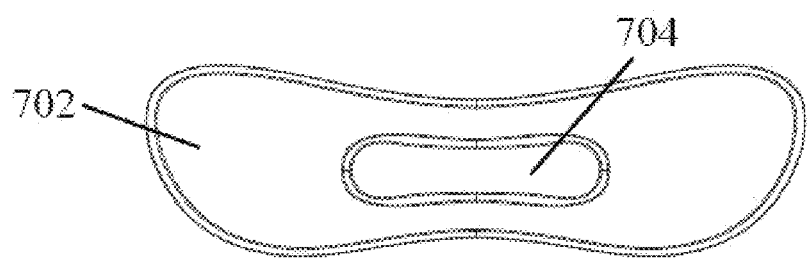
Figure 14F:
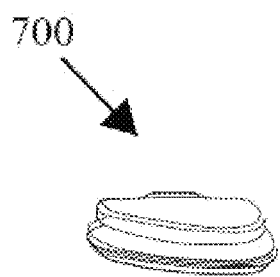
Figure 14G:
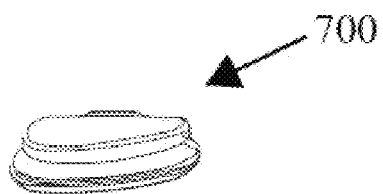
Figure 15:
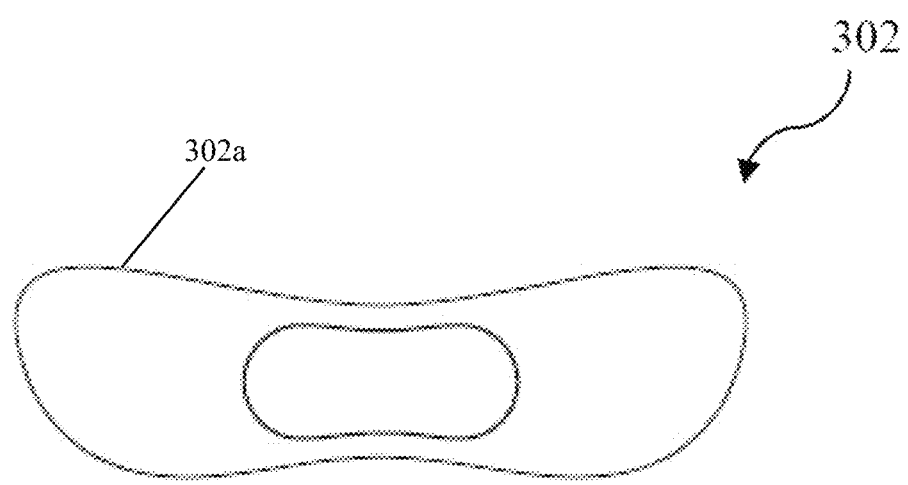
FIG. 15 is a bottom view of a sensor device of FIG. 12.

FIGS. 12, 13, and 15 illustrate embodiments of the sensor device 302, which may be formed to be flexible in one or multiple directions. The sensor device 302 can be of any height, width, or depth that will allow the sensor device 302 to be connectable with an associated carrier 304 (e.g., 2.5 inches in length and 0.72 inches in height). In the embodiments depicted in FIGS. 12, 13, and 15, the sensor device 302 has curved contours, which define the outer edges of the device 302. In the embodiment shown in FIG. 13, the sensor device 302 can be manufactured so as to be substantially linear or uncurved in an originating position and flexible in an upward and/or downward manner, if desired, to contour toward the shape of a user's body.

Another embodiment of a sensor device 700 is shown in FIGS. 14a-14g. The sensor device 700 includes a surface 704 that can be placed against a user's skin to obtain a temperature reading. The sensor device 700 can be manufactured so as to be curved in an originating position. The sensor device 700 can be provided with any desired radius (e.g., 5.00 inches) depending on the desired curvature of the shape.

Alternatively, the base 702 can have any desired one-, two- or three-dimensional shape or contour. If the base 702 is made of injection molded plastic, for example, the mold can be configured to produce a base 702 having the desired shape. As another example, a formable material, such as a thermoplastic sheet or metal, can be formed into the desired shape by using a die or former. The base 702, and thereby the sensor device 700, can therefore be shaped and/or contoured for a specific part of the body, if desired.

Embodiments of the carrier 304, in which the sensor device 302 is arranged, are illustrated in FIGS. 16-20. The carrier 304 can be of any height, width, or depth that can accommodate an associated sensor device 302 (e.g., 2.8 inches in length and 0.97 inches in height).

Figure 16:
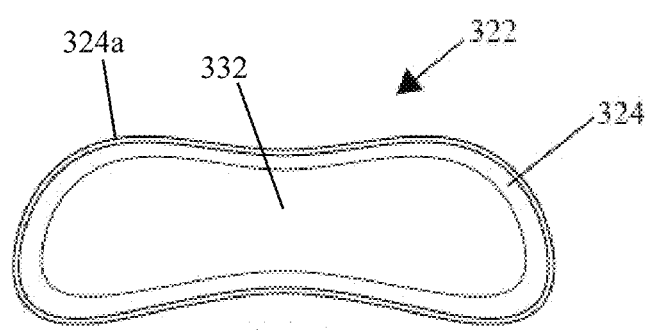
FIG. 16 is a top view of a frame of the carrier, which is included in the assembly of FIG. 10.

FIG. 16 illustrates an embodiment of a carrier frame 322 of the carrier 304 with contoured sidewalls 324. The contoured sidewalls 324 define an outer periphery and an opening 332 in which the sensor device 302 is held. The frame 322 can be manufactured from any known material, e.g., plastic, metal, silicone or rubber that is bendable so as to conform to a user's temple, arm or other body part on which a temperature reading may be desired. Additionally, any known process, such as thermoforming, can be utilized to for the carrier frame 322.

Figure 17:
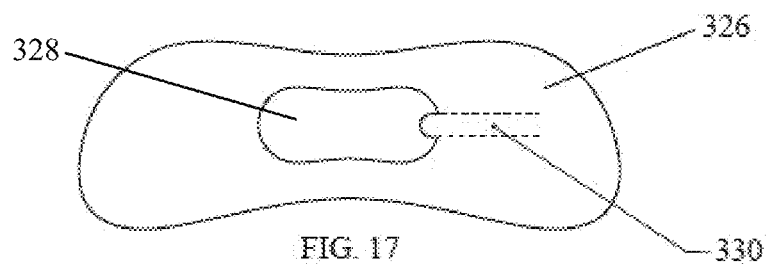
FIG. 17 is a top view of an adhesive layer, which is affixable to the carrier frame of FIG. 16.

FIG. 17 illustrates an adhesive layer 326 that is fastenable to the carrier frame 322. The adhesive layer 326 includes an opening 328 that can be, for example, punched thru the adhesive layer, either prior to or during (by) assembly of the sensor unit 302 into the carrier (which can be assisted by previously perforating the adhesive layer 326), and a perforated strip 330, which extends from the adhesive layer 326 into the opening 328, engaging the sensor unit, helping maintain the sensor unit in the carrier 340. The strip 330 can to aid in removing the sensor device 302 from the carrier 304 after use by pulling the strip 330, which in turn applies a force to the sensor device 302 and helps to force the sensor device 302 from the carrier 304. The adhesive layer can contain an adhesive on the skin-contacting side thereof to adhere the carrier 304 to the skin. The adhesive layer 326 can also contain an adhesive on the side opposite the skin-contacting side to assist in holding the temperature sensor 302 in the carrier 304.

Figure 18:
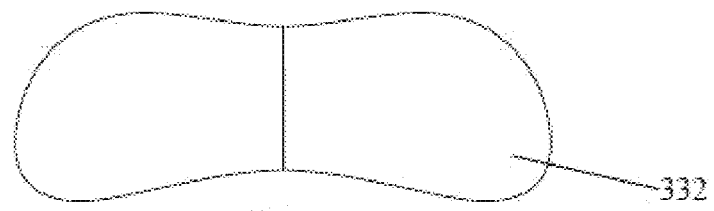
FIG. 18 is a top view of peel-off backing, which is removably affixed to the adhesive layer of FIG. 17.

FIG. 18 illustrates a peel-off backing 332 that is removably affixable to the structural adhesive layer 326, e.g., over the adhesive on the skin-contacting side. The peel-off backing 332 ensures that the adhesive layer 326 is not contaminated and remains tacky prior to use.

Figure 19:
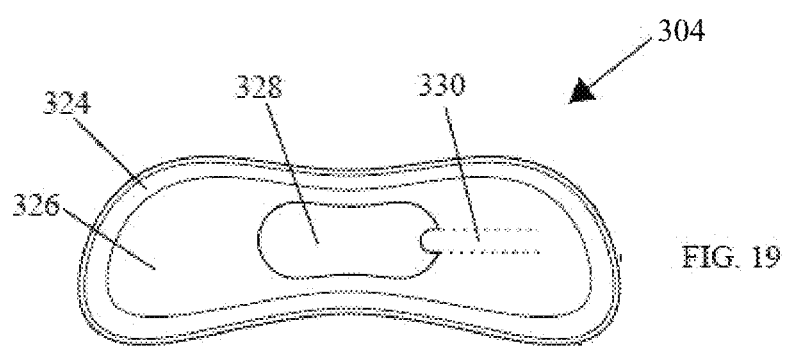
FIG. 19 is a top view of an assembled carrier, which includes the frame, adhesive layer, and peel-off backing.

FIG. 19 is a top view of an assembled carrier 304 that includes the frame 324, the adhesive layer 326 affixed to the frame 324, and the peel-off backing 332 affixed to the adhesive layer 326. The adhesive layer 326 can be affixed or connected to the frame 324 by any suitable means, e.g., adhesive, welding, etc. to form the carrier 304.

Figure 20:
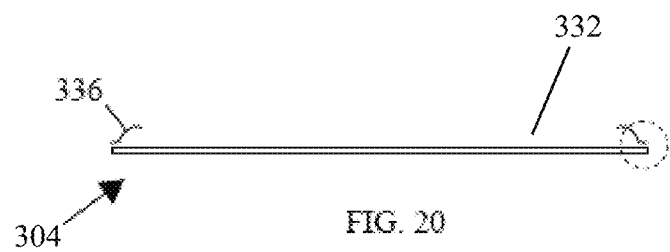
FIG. 20 is a cross-sectional side view of the carrier assembly.
Figure 24:
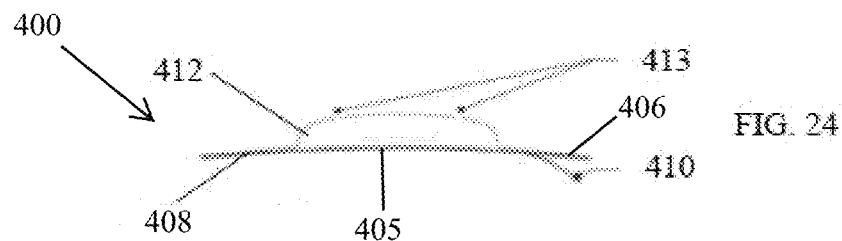
FIG. 24 is a side view of the temperature sensor assembly of FIG. 22.
Figure 25:
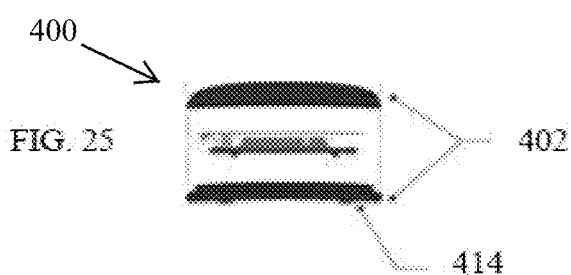
FIG. 25 is an exploded view of the sensor device of FIG. 22.

FIG. 20 illustrates a cross-sectional view of the carrier 304. As shown, contoured sidewalls 336 of the frame 324 define a groove or opening 332 in which the sensor 302 is arranged and secured, for example, by press-fit, as shown in FIGS. 11a-11b. For example, sidewalls 336 are configured so that the opening 332 is smaller than the base 302a of the temperature sensor 302. Thus, the sidewalls 336 define an interference with the base 302a. In order to engage the temperature sensor 302 into the carrier 304, the sidewalls are configured with a flexibility, e.g., and elastically-deformable material such as plastic, metal, rubber, silicone, etc., so as to elastically deform the sidewalls 336 and the opening 332 to the size of the base 302, e.g., by pressing the base 302a toward the opening 332, allowing the base 302a to pass through the opening 332 and into the carrier 304. As seen in FIGS. 11a and 11b, for the example, once the base 302a passes into the opening 332, the sidewalls 336 elastically return to or nearly to the original shape, retaining the base 302a between the adhesive layer 326 and the sidewalls 336. Similar to as discussed above with respect to the carrier 14, the sidewalls 336 can be formed of a material and configured so that the temperature sensor 302 and the carrier 304 can be assembled without excessive force but with sufficient force to securely retain the temperature sensor in the carrier.

FIG. 21 depicts the sensor assembly 300 affixed to a child for use. As discussed above, the assembly 300 can be contoured, either in an original configuration or through flexibility of the temperature sensor 302 and/or carrier 304, to substantially conform to the child's body part—the temple in this embodiment.

Figure 26:
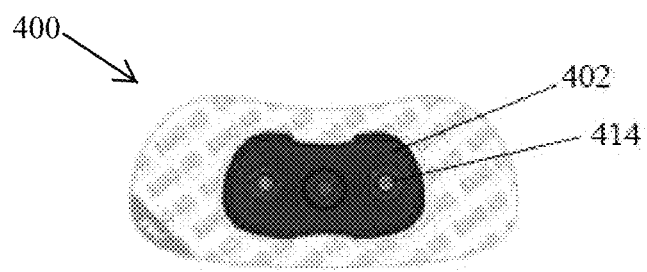
FIG. 26 is a bottom view of the temperature sensor assembly of FIG. 22.

FIGS. 22-26 depict another embodiment of a temperature sensor assembly 400, which includes a sensor device 402 and a carrier 404, similar to assembly 300, sensor device 302 and carrier 304. The carrier 404 is comprised of a frame 405, a single-sided breathable fabric 406 arranged on a first side of the frame 405, an adhesive layer 408 affixed to a second side of the frame, and a peel-off backing 410 affixed to the adhesive layer 408. The carrier 404 also includes an opening therein configured for receiving the sensor device 402 therethrough. A transparent protrusion 412 that has ventilation openings 413 extends across the opening in the carrier 404. The protrusion is configured to accommodate at least part to of the sensor device 402. The sensor device 402 includes a plurality of thermistors 414 extending from a base of the device 402. As best seen in FIG. 26, when arranged in the protrusion 412 of the carrier 404, the thermistors 414 extend past the carrier 404 in order to engage the user's skin.

As shown in an embodiment in FIGS. 27 and 28, the sensor device 402 is attachable to an adjustable armband 416 for attachment to a user's arm, to measure the body temperature at that location.

Figure 29:
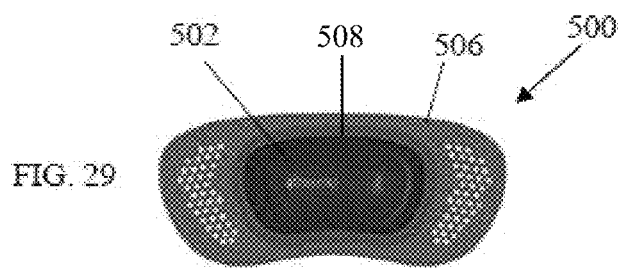
FIG. 29 is a top view of another embodiment of a temperature sensor assembly, which includes a sensor device and a carrier.
Figure 30:
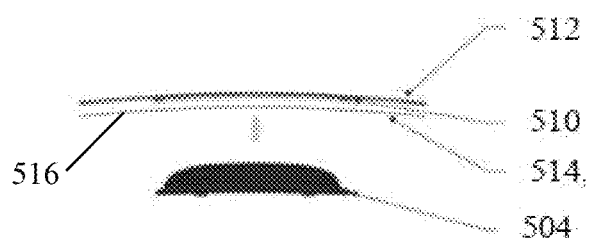
FIG. 30 is a schematic view of the assembly of the temperature sensor assembly of FIG. 29.
Figure 31:
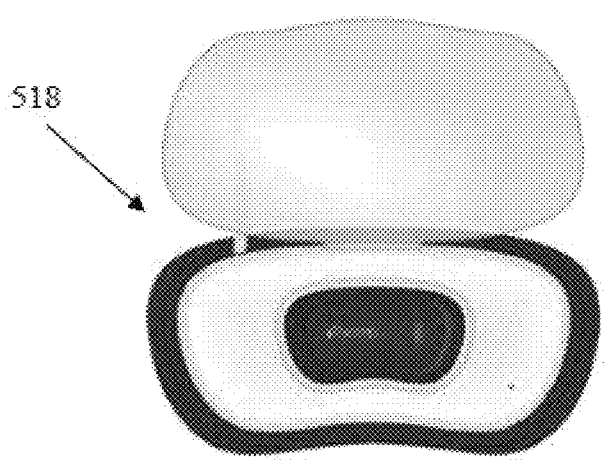
FIG. 31 is a top view the temperatures sensor of FIG. 22 mounted in a charger and the sensor and charger sitting in a base, with the charger cover in an open position.
Figure 32:
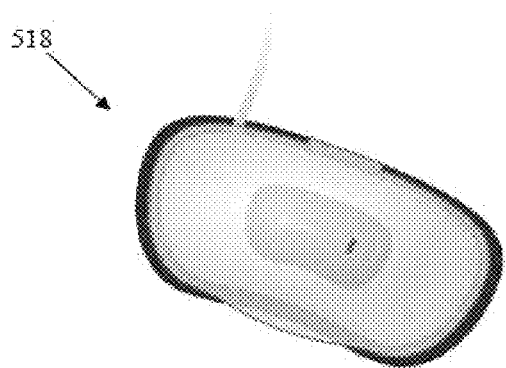
FIG. 32 is a top view of the charger, sensor and base assembly of FIG. 31 with the charger cover in a closed position.
Figure 33:
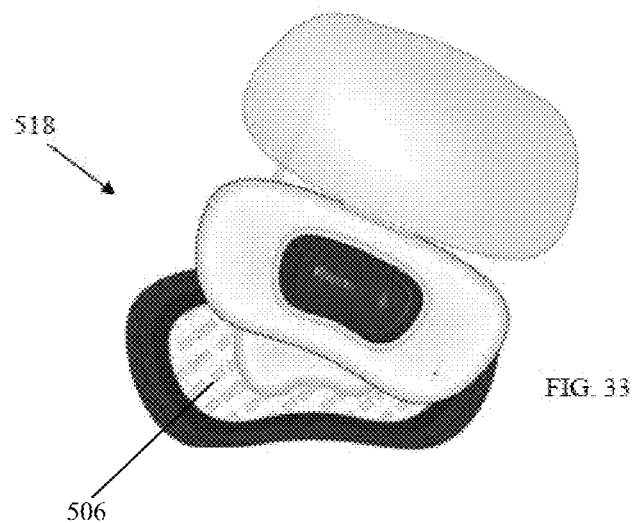
FIG. 33 is a top view of the charger and sensor assembly of FIG. 31 removed from the base and showing a storage compartment in the base containing an additional carrier.

FIGS. 29 and 30 illustrate yet another embodiment of a temperature sensor assembly 500. The assembly 500 comprises a sensor device 502, similar to sensor devices 302, 402, which includes a plurality of thermistors 504 protruding therefrom and a carrier 506, which has an opening 508 therein and is comprised of a frame 510, a layer of soft, breathable material 512 arranged on a first side of the frame 510, an adhesive layer 514 arranged on a second side of the frame 510 with a peel-off backing 516 protecting the adhesive properties of the adhesive layer 514. FIGS. 31-33 depict an embodiment of a charging device 518, similar to charging system 54 described above, that can be used to charge the sensor device 502 and store carrier 504.

Figure 34:
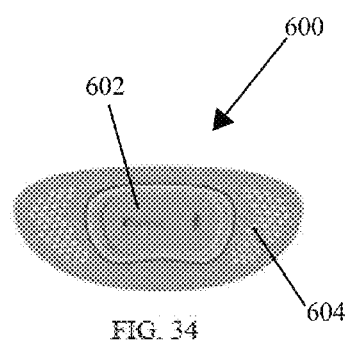
FIG. 34 is a top view of another embodiment of a temperature sensor assembly, which includes a sensor device and a carrier.

FIG. 34 depicts a further embodiment of a temperature sensor assembly 600, which includes a sensor device 602 and a carrier 604, similar to carrier 506 but having a different shape and color. The carrier 604 is shaped for use on a different part of the body as carrier 506. Those of ordinary skill in the art should understand that the carrier can be shaped and configured as desired, including, for example, as suitable for use on a particular body part.

As may be recognized by those of ordinary skill in the pertinent art based on the teachings herein, numerous changes and modifications may be made to the above-described and other embodiments of the present invention without departing from its scope as defined in the appended claims. In addition, like parts can be used in any and all embodiments without departing from the scope of the embodiment. Furthermore, though the invention may be used for body temperature measurement, it should be understood that the invention may be utilized for other applications as well, such as, for example, measurement of body mass index, calories burned, or distance walked per day. Accordingly, this detailed description of embodiments is to be taken in an illustrative as opposed to a limiting sense.

What is claimed is:

1. An apparatus for sensing body temperature and wirelessly communicating measured data to at least one electronic device, the apparatus comprising:
    a sensor device having a housing base, a housing cover releasably mounted to the housing base so as to permit removal of the housing cover from and re-attachment of the housing cover to the housing base, and components within one or more of the housing base or the housing cover configured for sensing body temperature and wirelessly communicating the measured data, said components including a temperature sensor, a power supply, a microprocessor, and a transmitter and receiver.

2. The apparatus according to claim 1, further comprising at least one light source.

3. The apparatus according to claim 2, wherein the at least one light source is an LED.

4. The apparatus according to claim 1, wherein the temperature sensor comprises a thermistor or a thermocouple.

5. The apparatus according to claim 1, wherein the power supply comprises a battery.

6. The apparatus according to claim 5, wherein the battery is disposable.

7. The apparatus according to claim 5, wherein the battery is rechargeable.

8. The apparatus according to claim 1, wherein the power supply is supplied via a power cord.

9. The apparatus according to claim 8, wherein the power supply is direct current.

10. The apparatus according to claim 8, wherein the power supply is alternating current.

11. The apparatus according to claim 1, wherein the microprocessor includes embedded software and dynamic memory storage.

12. The apparatus according to claim 1, wherein the transmitter and the receiver are adapted to communicate with the at least one electronic device via at least one of: R-F communication, infrared communication, Bluetooth communication, and Wi-Fi communication.

13. The apparatus according to claim 1, wherein the at least one electronic device is one or more of: a smart phone, a tablet, a mobile computer or a desktop computer.

14. The apparatus according to claim 1, further comprising a flexible carrier having an aperture therein, wherein the aperture is configured to engage the sensor device and the aperture releasably retains the sensor device to the carrier within the aperture.

15. The apparatus according to claim 14, wherein the housing cover has a peripheral projection extending therefrom and the housing base has a peripheral groove in which the peripheral projection is engageable to define between the housing cover and housing base a peripheral channel.

16. The apparatus according to claim 15, wherein the sensor device is retained in the aperture of the carrier by the peripheral channel.

17. The apparatus according to claim 15, wherein the housing base has a peripheral lip that extends from the peripheral groove and the sensor device is retained via the peripheral lip on the carrier.

18. The apparatus according to claim 15, wherein the housing base has a peripheral lip that extends from the peripheral groove and the sensor device is retained by the peripheral lip on the carrier and the peripheral channel.

19. The apparatus according to claim 14, wherein the sensor device and the carrier are configured to provide a press-fit or snap-fit engagement of the sensor device and the carrier by applying force to one or more of the carrier or the sensor device relative to the other, thereby elastically deforming the aperture and allowing the sensor device to pass into the aperture.

20. The apparatus according to claim 14, wherein the carrier is comprised of breathable material.

21. The apparatus according to claim 14, wherein the carrier includes a frame.

22. The apparatus according to claim 14, wherein the carrier has an adhesive layer with a first side and a second side, the first side being affixed to the frame and the second side being removably affixable to a user.

23. The apparatus according to claim 22, wherein the carrier includes a backing layer, which is affixable to the adhesive layer for protection of the adhesive layer from an environment prior to use.

24. The apparatus according to claim 22, wherein the housing base has a protrusion in which the temperature sensor is arranged and the protrusion is contactable with a user to obtain a body temperature reading of the user.

25. A kit comprising:
a sensor device having a housing base, a housing cover releasably mounted to the housing base so as to permit removal of the housing cover from and reattachment of the housing cover to the housing base, and components within one or more of the housing base or the housing cover configured for sensing body temperature and wirelessly communicating the measured data, said components including a temperature sensor, a power supply, a microprocessor, and a transmitter and receiver;
a carrier having an aperture therein, wherein the aperture is configured to engage the sensor device and releasably retain the sensor device to the carrier within the aperture; and
a charging unit adapted to charge the power supply.

26. The kit according to claim 25, wherein the charging unit comprises a charging cover, a charging base, a port within the charging base for fittingly receiving the device therein, and a power cord.

27. The kit according to claim 26, wherein the power cord is connectable to at least one of a wall outlet and a USB device.

28. The kit according to claim 25, wherein the charging unit includes a storage unit for storing the carrier.

29. A method for sensing body temperature and wirelessly communicating measured body temperature to at least one electronic device, the method comprising the steps of:
communicatingly connecting a device configured to sense body temperature wirelessly to the at least one electronic device;
inserting the device into a carrier having an aperture therein, wherein the aperture is configured to engage the sensor device and releasably retain the sensor device to the carrier within the aperture;
attaching the device to a user;
measuring the body temperature of the user;
transmitting the measured body temperature of the user measured wirelessly from the device to the at least one electronic device; and
displaying the temperature on the at least one electronic device.

30. The method according to claim 29, wherein the temperature measured is displayed in an application installed on the at least one electronic device.

31. The method according to claim 29, further comprising the step of transmitting data from the at least one electronic device to the device sensing body temperature.

32. The method according to claim 31, wherein the data comprises measurement instructions.

33. The method according to claim 29, wherein the body temperature measured is wirelessly transmitted from the sensing device to one or more of: a smart phone, a tablet, a mobile computer and a desktop computer.

34. A method of assembling a sensing device and a carrier for sensing body temperature and wirelessly communicating measured data to at least one electronic device, the method comprising:
providing a sensor device adapted to measure body temperature;
providing a carrier having an opening therein, wherein the opening is configured to engage the sensor device and releasably retain the sensor device to the carrier within the opening; and
arranging the sensor device in the opening of the carrier.

35. The method of claim 34, wherein the arranging step comprises press fitting or snap-fitting the sensor device into the opening by applying force to one or more of the carrier or the sensor device relative to the other, thereby elastically deforming the opening and allowing the sensor device to pass into the opening.

36. The method of claim 34, wherein the carrier has a perforated tab extending into the opening and engaging the sensor device and the method further comprises the step of pulling the tab to disengage the tab from the sensor device and release the sensor device from the carrier.

37. The kit according to claim 28, wherein the storage unit is configured to store at least one additional of said carrier.

38. An apparatus for sensing body temperature and wirelessly communicating measured data to at least one electronic device, the apparatus comprising:
- a sensor device having a housing base, a housing cover releasably mountable to the housing base, and components for sensing body temperature and wirelessly communicating the measured data, including a temperature sensor, a power supply, a microprocessor, and a transmitter and receiver;
- a flexible carrier having an aperture therein for releasably retaining the sensor device;
- wherein the housing cover has a peripheral projection extending therefrom and the housing base has a peripheral groove in which the peripheral projection is engageable; and one or more of:
  (i) the peripheral groove and the peripheral projection are engageable to define between the housing cover and housing base a peripheral channel, wherein the sensor device is retained in the aperture of the carrier by the peripheral channel; or
  (ii) the housing base has a peripheral lip that extends from the peripheral groove and the sensor device is retained via the peripheral lip on the carrier.

39. A method of assembling a sensing device and a carrier for sensing body temperature and wirelessly communicating measured data to at least one electronic device, the method comprising:
- providing a sensor device adapted to measure body temperature;
- providing a carrier having an opening configured to retain the sensor device therein; and
- arranging the sensor device in the opening of the carrier;
- wherein the carrier has a tab extending into the opening and engaging the sensor device; and
- the method further includes pulling the tab to disengage the tab from the sensor device and release the sensor device from the carrier.

* * * * *